United States Patent [19]
Bianchi

[11] Patent Number: 5,641,628
[45] Date of Patent: Jun. 24, 1997

[54] NON-INVASIVE METHOD FOR ISOLATION AND DETECTION OF FETAL DNA

[75] Inventor: Diana W. Bianchi, Brookline, Mass.

[73] Assignee: Children's Medical Center Corporation, Boston, Mass.

[21] Appl. No.: 338,279

[22] Filed: Nov. 14, 1994

Related U.S. Application Data

[63] Continuation of Ser. No. 957,736, Oct. 7, 1992, abandoned, which is a continuation-in-part of Ser. No. 772,689, Oct. 7, 1991, which is a continuation-in-part of Ser. No. 706,393, May 28, 1991, abandoned, which is a continuation-in-part of Ser. No. 436,057, Nov. 13, 1989, abandoned.

[51] Int. Cl.$^6$ .......................... C12Q 1/68; G01N 33/48; G01N 33/53
[52] U.S. Cl. .......................... 435/6; 435/91.2; 435/7.24; 435/7.25; 436/63; 935/78
[58] Field of Search .......................... 435/6, 91.2, 7.24, 435/7.25; 935/77, 78; 536/24.31, 25.4; 436/63

[56] References Cited

U.S. PATENT DOCUMENTS

| | | | |
|---|---|---|---|
| 4,190,535 | 2/1980 | Luderer et al. | 210/83 |
| 4,675,286 | 6/1987 | Calenoff | 435/7 |
| 4,800,159 | 1/1989 | Mullis et al. | 435/172.3 |

FOREIGN PATENT DOCUMENTS

| | | |
|---|---|---|
| WO90/06509 | 6/1990 | WIPO. |
| WO91/08304 | 6/1991 | WIPO. |

OTHER PUBLICATIONS

Brison et al, Molecular & Cellular Biology, V. 2, May 1982, pp. 578–587.
Hames et al, Nucleic Acid Hybridisation, 1985, RL Press, pp. 190–193.
Bianchi et al., "Isolation Of Fetal DNA From Nucleated Erythrocytes In Maternal Blood", *PNAS USA*, 87:3279–3283 (May 1990).
Bianchi, "Demonstration Of Fetal Gene Sequences In Nucleated Erythrocytes Isolated From Maternal Blood", *Amer. J. Human Genetics*, 45(4):A252 (Oct. 17, 1989).
Raeburn, "Fetal Cells Isolated In Women's Blood", Hickory, North Carolina *Daily Record* The Associated Press (Jul. 28, 1989).
Bianchi et al., "Isolation Of Male Fetal DNA From Nucleated Erythrocytes (NRBC) In Maternal Blood", *Pediatric Research*, 25(4):139A, Abstract No. 818 (May 1989).
Bianchi et al., "Direct Hybridization To DNA From Small Numbers Of Flow Sorted Nucleated Newborn Cells", *Cytometry*, 8:197–202 (1987).
Schroder, "Transplacental Passage Of Blood Cells", *J. Medical Genetics*, 12:230–242 (Sep. 1975).

(List continued on next page.)

*Primary Examiner*—Stephanie W. Zitomer
*Assistant Examiner*—Carla Myers
*Attorney, Agent, or Firm*—Lahive & Cockfield; Elizabeth A. Hanley

[57] ABSTRACT

A method of detecting the presence or absence of a fetal DNA sequence of interest in fetal DNA derived from a sample of peripheral blood obtained from a pregnant woman is described. The method involves obtaining a sample of peripheral blood from a pregnant woman, treating the sample of peripheral blood such that the fetal DNA present in the fetal nucleated cells is made available for detection and detecting the presence or absence of the fetal DNA sequence of interest in the available fetal DNA. The proportion of fetal nucleated cells present in the sample of peripheral blood can be increased forming a sample enriched in fetal nucleated cells prior to the detection step. The fetal DNA sequence of interest can be detected by treating the peripheral blood sample such that fetal DNA present in the sample is made available for hybridization with a DNA probe and subsequently contacting the available fetal DNA with a DNA probe hybridizable to fetal DNA of interest under hybridization conditions. The presence or absence of hybridization between the DNA probe and the fetal DNA of interest is detected as an indication of the presence or absence of the fetal DNA of interest.

26 Claims, 22 Drawing Sheets

OTHER PUBLICATIONS

Jan et al., "Fetal Erythrocytes Detected And Separated From Maternal Blood By Electronic Fluorescent Cell Sorter", *Texas Reports On Biology and Medicine*, 31(3):575 (Fall 1973).

Cohen and Zuelzer, "Mechanisms Of Isoimmunization", *Blood*, 30(6):796–804 (Dec. 1967).

Clayton et al., "Fetal Erythrocytes In The Maternal Circulation Of Pregnant Women", *Obstetrics and Gynecology*, 23(6):915–919, (Jun. 1964).

International Search Report for PCT/US/9006623 (Feb. 22, 1991).

Mueller et al., "Isolation Of Fetal Trophoblast Cells From Peripheral Blood Of Pregnant Women", *Lancet*, 336:197–200 (Jul. 28, 1990).

Lo et al., "Prenatal Sex Determination By DNA Amplification From Maternal Peripheral Blood", *Lancet*, 1363–1365 (Dec. 9, 1989).

Adinolfi et al., "Gene Amplification To Detect Fetal Nucleated Cells In Pregnant Women", *Lancet*, 328–329 (Aug. 5, 1988).

Gray et al., "Prenatal and Perinatal Genetics", *Amer. J. Human Genetics*, 43(3), Supp.:A252, No. 0935 (Sep. 1988).

Covone et al., "Analysis Of Peripheral Maternal Blood Samples For The Presence Of Placenta–Derived Cells Using Y–Specific Probes And McAB H315", *Prenatal Diagnosis*, 8:591–607 (1988).

Mueller et al., "Identification Of Extra Villous Trophoblast Cells In Human Decidua Using An Apparently Unique Murine Monoclonal Antibody To Trophoblast", *Histochemical Journal*, 19:288–296 (1987).

Butterworth et al., "Human Cytotrophoblast Populations Studied By Monoclonal Antibodies Using Single And Double Biotin–Avidin–Peroxidase Immunocytochemistry", *Chem. Abstracts*, 103:192486c (1985).

Covone et al., "Trophoblast Cells In Peripheral Blood From Pregnant Women", *Lancet*, 841–843 (Oct. 13, 1984).

Kulozik and Pawlowitzki, "Fetal Cells In The Maternal Circulation: Detection By Direct AFP–Immunofluorescene", *Human Genetics*, 62:221–224 (1982).

Iverson et al., "Detection And Isolation Of Fetal Cells From Maternal Blood Using The Fluorescence–Activated Cell Sorter (FACS)*", *Prenatal Diagnosis*, 1:61–73 (1981).

Ockenhouse et al., "Platelet and Monocyte Activation", *J. Clin. Invest.*, 84:468–475 (Aug. 1989).

Loken et al., "Flow Cytometric Analysis Of Human Bone Marrow: I. Normal Erythroid Development", *Blood*, 69(1):255–263 (Jan. 1987).

Berenson et al., "Positive Selection Of Viable Cell Populations Using Avidin–Biotin Immunoadsorption", *J. Immun. Methods*, 91:11–19 (1986).

Kumar et al., "Cell Separation: A Review", *Pathology*, 16:53–62 (1984).

Basch et al., "Cell Separation Using Positive Immunoselective Techniques", *J. Immun. Methods*, 56:269–280 (1983).

Bigbee et al., "Monoclonal Antibodies Specific for the M– and N–Forms of Human Glycophorin A" *Molecular Immunology*, 20(12):1353–1362.

Berenson et al., "Antigen CD34+ Marrow Cells Engraft Lethally Irradiated Baboons", *J. Clin. Invest.*, 81:951–955 (Mar. 1988).

Kogan et al., "An Improved Method For Prenatal Diagnosis Of Genetic Diseases By Analysis Of Amplified DNA Sequences", *New England J. Med.*, 317(16):985–990 (Oct. 15, 1987).

Berenson et al., "Cellular Immunoabsorption Using Monoclonal Antibodies", *Transplantation*, 38(2):136–143 (Aug. 1984).

Simpson et al., "Genetics In Obstetrics And Gynecology", Chapter 6, pp. 116–117 (1982).

Lipinski et al., "Human Trophoblast Cell–Surface Antigens Defined By Monoclonal Antibodies", *PNAS USA*, 78(8):5147–5150 (Aug. 1981).

Payne, "The Development And Persistence of Leukoagglutinins In Parous Women", *Blood*, 19(4):411–424 (Apr. 1962).

Herzenberg et al, "Fetal cells in the Blood of Pregnant women: Detection and Enrichment by Fluorescence–Activated Cell Sorting", *PNAS USA*, vol. 76, No. 3, pp. 1453–1455, (Mar. 1979).

Watchel et al., "Fetal cells in the maternal circulation: isolation by multiparameter flow cytometry and confirmation by polymerase chain reaction", *Human Reproduction*, vol. 6, No. 10, pp. 1466–1469, (1991).

Chueh et al., "The search for fetal cells in the maternal circulation", *J. Perinat. Med.* 19, pp. 411–419 (1991).

Chueh et al. "Prentatal Diagnosis Using Fetal Cells in the Maternal Circulation", *Seminars in Perinatology* vol. 14, No. 6 (Dec. 1990), pp. 471–482.

Holzgreve et al. "Fetal Cells in the Maternal Circulation" *The Journal of Reproductive Medicine*, vol. 37, No. 5 (May 1992).

Simpson et al., "Isolating and Analyzing Fetal Cells in Maternal Blood: Current Status (1992)", *Early Fetal Diagnosis: Recent Progress and Public Health Implications*, Karolinum–Charles University Press, Prague 1992.

Ganshirt–Ahlert et al., "Magnetic cell sorthing and the transferrin receptor as potential means of prenatal diagnosis from maternal blood", *Am. J. Obstet, Gynecol.*, pp. 1350–1355 (May 1992).

Ried et al., "Multicolor fluorescence in situ hybridization for the simultaneous detection of probe sets for chromosomes 13, 18, 21, X and Y in uncultured amniotic fluid cells", *Human Molecular Genetics*, vol. 1, No. 5, pp. 307–313 (1992).

Klinger et al., "Rapid Detection of Chromosome Aneuploidies in Uncultured Amniocytes by Using Fluorescence In Situ Hybridization (FISH)", *Am. J. Hum. Genet.* 51:55–65 (1992).

Adinolfi, Matteo "On A Non–invasive Approach to Prenatal Diagnosis Based on the Detection of Fetal Nucleated Cells in Maternal Blood Samples", *Prenatal Diagnosis*, vol. 11, 799–804 (1991).

Becton–Dickinson Brochure entitled "Monoclonal Antibodies Detecting Human Antigens/Anti–Transferrin Receptor", Source Book Section 4.30 (1987).

Pharmacia Brochure entitled "Ficoll–Paque for in vitro isolation of lymphocytes".

GenTrak, Inc. Brochure entitled "GenTrak Monoclonal Antibodies for Flow Cytometry" (1989).

Amac, Inc. Price List, Jun. 1990.

"Noninvasive way is cited to detect Down syndrome in fetuses" *The Boston Globe*, Nov. 12, 1992, p. 8.

"Safer Test for Birth Defects is Reported" *New York Times*, Nov. 12, 1992, pp. A3 and A22.

Becton–Dickinson Brochure entitled "Monoclonal Antibodies Detecting Human Antigens" Source Book Sections 4–24, 4.25, 4.4 (1987).

Bianchi et al. (1990) "Detection of Fetal Nucleated Erythrocytes in First Trimester Maternal Blood Samples" *Early Fetal Diagnosis: Recent Progress and Public Health Impact*, Karolinum–Charles University Press, Prague, 1990.

Pembrey et al. "Maternal Synthesis of Hemoglobin F in Pregnancy" *The Lancet* (1973) pp. 1350–1354.

Lloyd et al., "Intrapartum Fetomaternal Bleeding in Rh–Negative Women" *Obstetrics and Gynecology*, vol. 56, No. 3, (1980) pp. 285–287.

Bickers et al., "Fetomaternal Transfusion Following Trauma" *Obstetrics and Gynecology*, vol. 61, No. 2 (1983) pp. 258–259.

Bianchi et al., "Possible Effect of Gestational Age on the Detection of Fetal Nucleated Erythrocytes in Maternal Blood" *Prenatal Diagnosis*, vol. 11, pp. 523–528 (1991).

Bertero et al., "Circulating Trophoblast Cells in Pregnancy Have Maternal Genetics Markers" *Prenatal Diagnosis*, vol. 8, pp. 585–590 (1988).

Schaffer's *Disease of the Newborn*, Fifth Edition, W.B. Saunders Company (1984) pp. 24–36.

Kawata et al., "Transcriptional Control of HLA–A, B, C Antigefn in Human Placental Cytotrophoblast Isolated Using Trophoblast and HLA–Specific Monoclonal Antibodies and the Fluorescence–Activated Cell Sorter" *J. Exp. Med.* vol. 160, 1984, pp. 633–651.

Bulmer et al., "Antigen Expression by Trophoblast Populations in the Human Placenta and Their Possible Immunobiological Relevance" *Placenta* (1985), 6, pp. 127–140.

"Researches find safer prenatal tests" *The Boston Herald*, Nov. 14, 1989.

"New test speeds detection of birth defects" *Boston Globe*, Oct. 8, 1991.

"IG Labs Licenses New Technology for Fetal Testing", *The Wall Street Journal*, Aug. 10, 1990.

"Birth defects detected with simple blood test" *USA Today*, Oct. 9, 1991.

"Prenatal blood test can signal genetic disorders", *Washington Times*, Oct. 9, 1991.

"A simpler, safer blood test for birth defects", *USA Today*, Nov. 14, 1989.

"Noninvasive Fetal Screening Technique Developed", *Harvard Medical Area*, May 3, 1990.

*Abstracts from 42nd Annual Meeting American Soc. Human Genetics*, Nov. 9–13, 1992, Nos. 1621, 1049, 1031, 1013, 996, 182, 181, 5.

Detection of Cord Blood Male DNA in
Reconstruction Experiments
(TfR antibody)

NON-INVASIVE METHOD FOR ISOLATION AND DETECTION OF FETAL DNA

FUNDING

Work described herein was supported by the National Institute of Health and Children's Hospital Medical Center.

This application is a continuation of application Ser. No. 07/957,736, filed on Oct. 7, 1992 (now abandoned), which is continuation-in-part of application Ser. No. 07/772,689 filed on Oct. 7, 1991, which is a continuation-in-part of application Ser. No. 07/706,393 filed on May 28, 1991 (now abandoned), which is a continuation-in-part of application Ser. No. 07/436,057, filed on Nov. 13, 1989 (now abandoned). The contents of all of the aforementioned applications are expressly incorporated by reference.

BACKGROUND

A variety of fetal cell types—platelets, trophoblasts, erythrocytes and leucocytes—cross the placenta and circulate transiently within maternal blood (Schroder, J., J. Med. Genet. 12:230–242 (1975); Douglas G. W. et al., Am. J. Obstet. Gynec., 78:960–973 (1959)). There have been numerous reports of efforts to separate fetal cells from maternal cells present in maternal blood, but none has been successful in isolating cells subsequently shown to contain fetal DNA. Distinguishing fetal cells from maternal cells has not been successful for several reasons, including the small number of fetal cells in a maternal blood sample and the fact that morphological differences are slight (e.g., trophoblasts are the only fetal cells which can be distinguished from maternal cells by morphology alone).

Others report screening the peripheral blood of pregnant women for cells of fetal origin. Fetal identification relied on the presence of a single cytogenetic marker, the Y chromosome. Lymphocytes with a putative "XY" karyotype were found in the maternal circulation as early as 14 weeks gestation (Walknowska, J., et al., The Lancet, 1119–1122 (1979)).

The availability of flow cytometry has led many to suggest that fetal cells could be obtained through the use of a flow cytometer and that such cells could be exploited for prenatal genetic diagnosis. However, although cells sorted in this manner have been said to be of fetal origin, based on analysis of cell surface antigens, morphology, or cytogenetic criteria, there has not been confirmation that the cells contain fetal DNA. A method by which fetal DNA could be obtained from maternal blood during pregnancy would be valuable, particularly if it made it possible to carry out prenatal diagnosis by a noninvasive technique.

DISCLOSURE OF THE INVENTION

The present invention is based, at least in part, on the discovery that fetal nucleated cells are present in the peripheral blood of a pregnant woman at a level which allows them to be useful in prenatal diagnostic methods. The method of the present invention is non-invasive because a peripheral blood sample from a pregnant woman, not fetal blood, is used as the source of the fetal DNA. The fetal DNA is derived from fetal nucleated cells present in the peripheral blood of a pregnant woman. The method of the present invention can be used to assess fetal characteristics (e.g. fetal sex and chromosomal abnormalities) or can be used to diagnose whether a fetus has a prenatal disease at an early stage of the gestational period. The non-invasive method of the present invention does not expose the fetus or mother to risks, e.g. infection, fetal injury, and miscarriage, associated with invasive methods such as amniocentesis.

The present invention pertains to a method of detecting the presence or absence of a fetal DNA sequence of interest in fetal DNA derived from a sample of peripheral blood obtained from a pregnant woman. The method involves obtaining a sample of peripheral blood from a pregnant woman, treating the sample of peripheral blood such that the fetal DNA present in the fetal nucleated cells is made available for detection and detecting the presence or absence of the fetal DNA sequence of interest in the available fetal DNA. The proportion of fetal nucleated cells present in the sample of peripheral blood can be increased forming a sample enriched in fetal nucleated cells prior to the detection step. The fetal DNA sequence of interest can be detected by treating the peripheral blood sample such that fetal DNA present in the sample is made available for hybridization with a DNA probe and subsequently contacting the available fetal DNA with a DNA probe hybridizable to fetal DNA of interest under hybridization conditions. The presence or absence of hybridization between the DNA probe and the fetal DNA of interest is detected as an indication of the presence or absence of the fetal DNA of interest.

The method of the present invention can be used to determine the sex of a fetus by contacting the peripheral blood sample from a woman pregnant with a fetus with a DNA probe hybridizable to fetal Y chromosomal DNA. The presence of hybridization between the DNA probe and the fetal Y chromosomal DNA can be detected as an indication of a male fetus or the absence of hybridization can be detected as an indication of a female fetus.

The method of the present invention also may be used for diagnosing a disease in a fetus. A sample of peripheral blood obtained from a woman pregnant with a fetus is contacted with DNA probe hybridizable to fetal DNA of interest associated with a disease under hybridization conditions. The presence or absence of hybridization between the DNA probe and the fetal DNA of interest is detected as an indication of whether the fetus has the disease.

The method of the present invention further can be used to detect a chromosomal abnormality in a fetus such as a chromosomal aneuploidy, e.g., trisomy 13, trisomy 18, or trisomy 21. A sample of peripheral blood from the woman pregnant with a fetus is obtained. The fetal nucleated cells are separated from the peripheral blood sample onto a solid support forming immobilized fetal nucleated material, e.g. metaphase or interphase nuclei. The immobilized fetal nucleated material is contacted with a DNA probe hybridizable to chromosomal fetal DNA of interest under hybridization conditions. The presence or absence of hybridization between the DNA probe and the chromosomal fetal DNA of interest is detected as an indication of the presence or absence of a chromosomal abnormality.

The method of the present invention further can be used to determine whether a pregnancy is at risk. Fetal blood hemhorrages into the maternal blood system typically occur when a pregnancy is at risk increasing the number of fetal cells present in the maternal blood. A peripheral blood sample can be obtained from a pregnant woman at a selected gestational age and the number of fetal cells present in the sample can be detected. This detected number of fetal cells can be compared to a known standard representative of the number of cells present at the selected gestational age during a normal pregnancy. The standard can be established by taking peripheral blood samples from a group of women at the selected gestational age believed to be having normal pregnancies.

Other aspects of this invention relate to methods of enriching the peripheral maternal blood sample and kits containing reagents used to conduct the described methods. These aspects are described in more detail below.

DETAILED DESCRIPTION OF THE INVENTION

Figure 1:
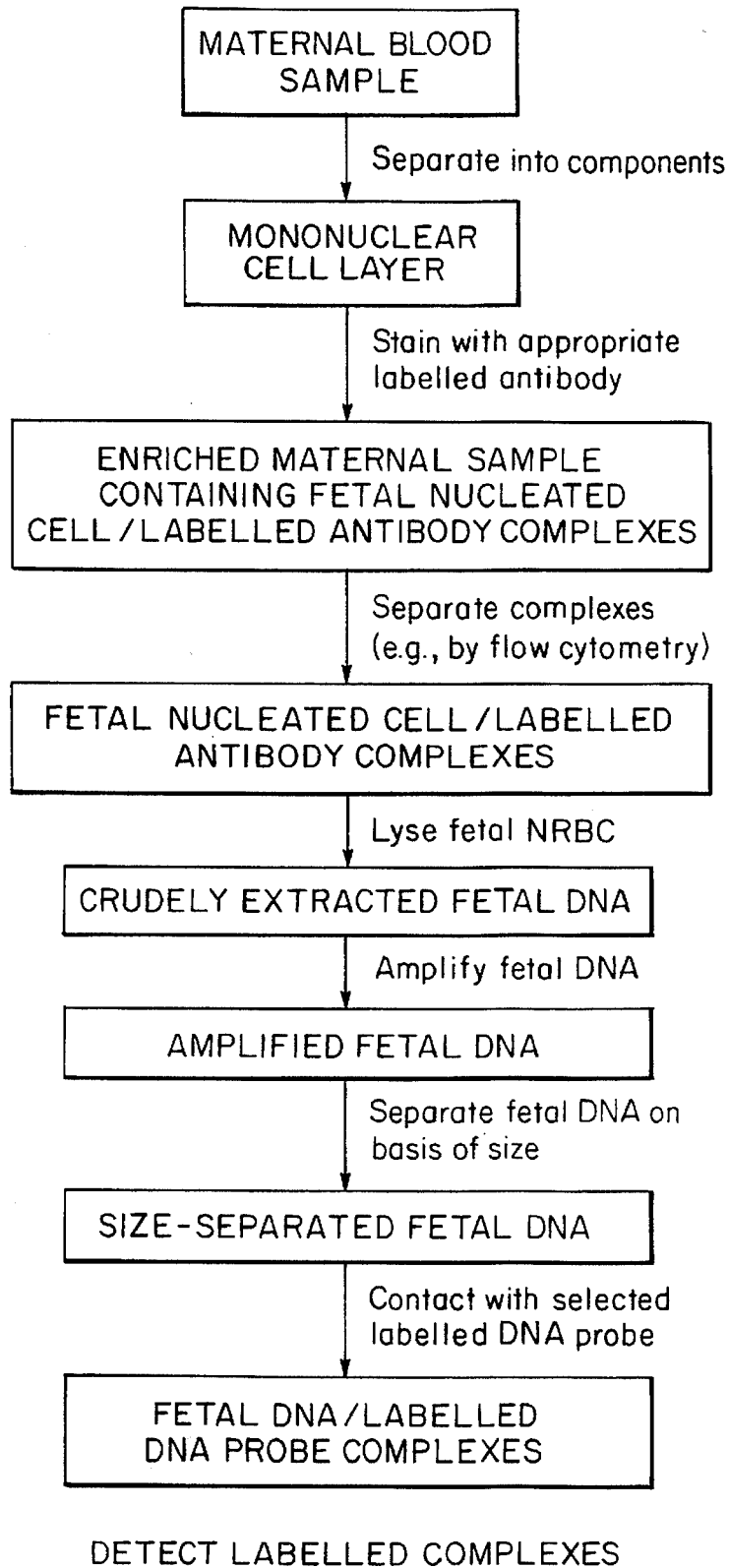
FIG. 1 is a schematic representation of the method of the present invention by which fetal nucleated cells are isolated from maternal cells and DNA within the fetal cells is assessed for the occurrence of a particular fetal DNA sequence.
Figure 2:
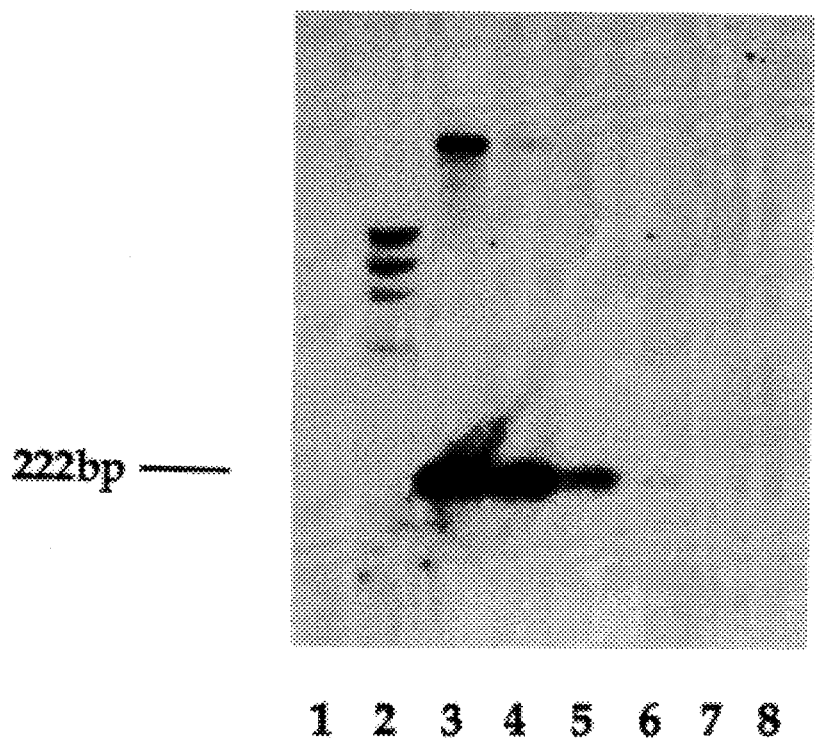
FIG. 2 is an autoradiograph of diluted male DNA amplified for 222 bp sequence. Lane 1: reagent control; lane 2: φX174 molecular weight standard; lane 3: 100 ng; lane 4: 10 ng; lane 5: 1 ng; lane 6: 200 pcg; lane 7: 10 pcg; lane 8: 1 pcg.
Figure 3:
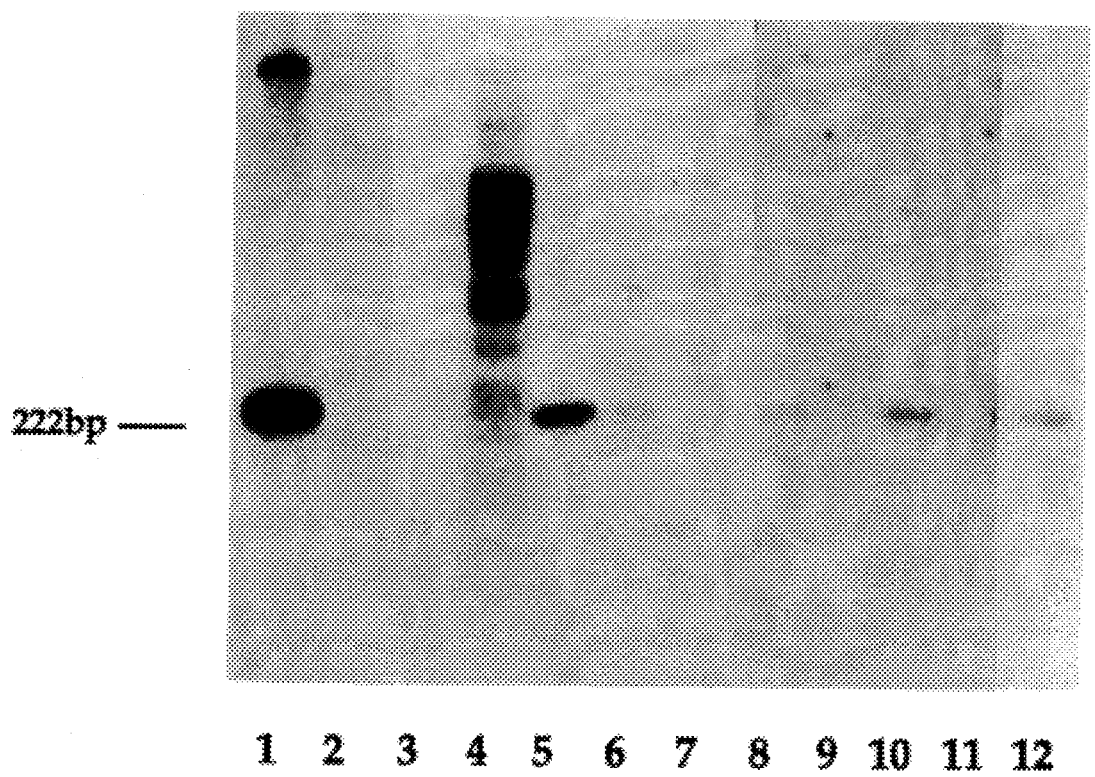
FIG. 3 is a composite autoradiograph of amplified patient DNA. Lane 1: 10 ng normal male; lane 2: 10 ng normal female; lane 3: reagent control; lane 4: φX174; lane 5: sorted cells from patient 1 (male fetus); lane 6: sorted cells from patient 2 (male fetus); lane 7: sorted cells from patient 3 (female fetus); lane 8: sorted cells from patient 6 (female fetus); lane 9: sorted cells from patient 7 (male fetus); lane 10: sorted cells from patient 8 (male fetus); lane 11: sorted cells from patient 9 (female fetus); lane 12: cord blood from female infant whose cells were prenatally sorted in lane 8.

The present invention relates to an in vitro method of separating or isolating fetal nucleated cells present in the blood of a pregnant woman (a maternal blood sample) from the pregnant woman's cells and of separating or isolating fetal DNA from maternal DNA. It further related to an in vitro method of prenatal detection and/or quantitation of selected fetal DNA in fetal DNA isolated from the maternal blood sample. The method provides a noninvasive approach to detect and/or quantitate fetal DNA, such as that associated with a disease or a condition whose assessment during gestation is desired. It also provides a noninvasive means by which the sex of a fetus can be determined.

In the present method, fetal nucleated cells are isolated from a maternal blood sample by means of a detectable material which binds to the fetal nucleated cells but not to maternal cells and is then separated from the maternal sample, resulting in separation of the fetal nucleated cells from the sample. The fetal nucleated cells can be any undifferentiated hematopoietic cell and, particularly, fetal nucleated erythrocytes. In one embodiment of the present method of isolation, at least one detectably labelled monoclonal antibody specific for an antigen present on fetal nucleated cells, but not for an antigen present on maternal cells, is combined with a maternal blood sample and, once bound to fetal nucleated cells, is separated from the maternal sample. Alternatively, at least one detectably labelled monoclonal antibody specific for an antigen present on maternal cells, but not for an antigen present on fetal nucleated cells is used. In a further embodiment, the two types of monoclonal antibodies are used.

In the case in which the detectable label is a fluorescent molecule, separation is carried out by means of flow cytometry, in which fluorescently-labelled molecules are separated from unlabelled molecules. This results in separation of fetal nucleated cells, such as fetal nucleated erythrocytes, from maternal cells and, thus, of fetal DNA from maternal DNA. That this separation has occurred can be verified using known techniques, such as microscopy or detection of fetal hemoglobin.

In one embodiment of the method of the present invention by which the occurrence of a selected DNA sequence or sequences (gene(s) or gene portion(s)) in fetal DNA is determined (detected and/or quantitated), the isolated fetal nucleated cells, such as fetal nucleated erythrocytes, are treated to render DNA present in them available for amplification. Amplification of DNA from fetal nucleated cells (fetal DNA) is carried out using a known amplification technique, such as the polymerase chain reaction (PCR). Amplified fetal nucleated cell DNA is subsequently separated on the basis of size (e.g., by gel electrophoresis) and contacted with a selected labelled probe, such as labelled DNA complementary to a selected DNA sequence (e.g., complementary to an abnormal gene or gene portion, or Y-specific DNA). Detection of the labelled probe after it has hybridized to fetal DNA results in detection of the sequence of interest in the fetal DNA. Quantitation of the hybridized labelled probe results in quantitation of the fetal DNA.

In a second embodiment of the present method of determining the occurrence of a selected DNA sequence (or sequences), cells isolated as described above are sorted onto a solid support, such as a slide, and screened for chromosomal abnormalities using in situ hybridization. In this embodiment, a selected nucleic acid probe, such as a labelled DNA probe for chromosomal DNA associated with a congenital abnormality, is combined with the fetal DNA, under conditions appropriate for hybridization of complementary sequences to occur. Detection and/or quantitation of the labelled probe after hybridization results in detection and/or quantitation of the fetal DNA to which the probe has hybridized.

The following is a description of the basis for the subject method; of the present method of isolating nucleated fetal cells present in the blood of a pregnant woman from maternal cells and, subsequently, separating fetal DNA from maternal DNA; and of the present method of prenatal determination of the occurrence (presence/absence or quantitation) of selected DNA in fetal cells.

Potential Sources of Fetal Genes

It has been determined that several types of fetal cells present in the blood of a pregnant woman are a source of fetal genes. In particular, it has been shown that fetal cells, such as nucleated erythrocytes (also referred to as fetal NRBC), and other undifferentiated hematopoietic precursor cells, such as erythroblasts, lymphoblasts and myeloblasts, can be isolated or separated from maternal blood. Fetal nucleated erythrocytes were particularly selected for sorting based on the following rationale:

1. In any given fetomaternal hemorrhage, no matter how small, the ratio of fetal erythrocytes to fetal lymphocytes should remain the same as in whole fetal blood; thus, there would be 1,000 times as many red cells as white cells available for analysis.
2. Normal pregnant females do not usually have circulating NRBC; therefore, an isolated NRBC would a priori have a greater chance of being fetal in origin.
3. The majority of pregnancies are blood group compatible, which means that the "transfused" NRBC would probably be tolerated by the mother and remain in her circulation.
4. Because they are nucleated, the NRBC contain a full complement of fetal genes.

It has been shown that fetal nucleated erythrocytes, as well as other types of fetal cells, can be isolated or separated from maternal blood and that DNA present in the isolated fetal cells can be used to assess fetal characteristics (e.g., sex, presence or absence of chromosomal abnormalities).

Advances in Molecular Biology Applied to Fetal Cell Sorting

Recent advances in molecular biology have had an enormous impact on the feasibility of fetal cell identification. For example, fluorescent in situ hybridization can be used for this purpose.

The development of the polymerase chain reaction (PCR) (Mullis, K., et al., *Cold Spring Harb. Symp. Quant. Biol.*, 51:263–272 (1986), with its capacity for DNA analysis from a single cell (Li, H., et al., *Nature*, 355:414–417 (1988); Handyside, A. H., et al., *Lancet* 1:347–349 (1989)), has eliminated the technical problems associated with the small number of fetal cells in maternal blood. It makes DNA diagnosis from a single cell possible.

As described below, fetal nucleated erythroblasts have been shown to be present in blood obtained from pregnant women, thus making maternal blood a useful/reliable potential source of fetal DNA; fetal nucleated cells have been distinguished from maternal cells on the basis of surface antigenic characteristics, thus making it possible to separate the two cell types from one another; and fetal DNA present in the separated fetal nucleated cells has been analyzed and characterized.

Detection of Fetal Gene Sequences in Maternal Blood

One of the first steps in developing the present method of isolating fetal nucleated cells from the maternal blood supply was identification of monoclonal antibodies that permit identification and separation of fetal cells from maternal cells present in blood obtained from a pregnant woman. This has been done, as described in detail in the Examples. As a result, it has been determined that monoclonal antibodies which recognize maternal leucocytes and monoclonal antibodies which recognize fetal cell surface antigens are useful in separating maternal and fetal cells. The following is a brief description of monoclonal antibodies which have been shown to be useful in separating fetal nucleated cells from maternal cells present in a maternal blood sample. However, other monoclonal antibodies which distinguish between fetal and maternal cells on the basis of surface antigenic differences, can also be used in the present method.

The present method requires the use of at least one type of antibody which is specific for (or recognizes) a surface antigen present on fetal nucleated cells, for a surface antigen present on maternal cells, but not specific for both. That is, the present method can be carried out using one or more antibody which distinguishes fetal nucleated cells from maternal cells. The present method can be carried out using whole blood or blood treated or processed to enrich for (increase the concentration of) fetal nucleated cells.

Described below is the selection and successful use of monoclonal antibodies which distinguish fetal nucleated erythrocytes from maternal cells. It is to be understood, however, that in a similar manner, monoclonal antibodies which make it possible to select for another fetal nucleated cell type (or types) can be identified and used in the present method to separate fetal nucleated cell types from maternal cells (and, thus, fetal DNA sources from maternal DNA).

Initial efforts focused on the elimination of contaminating maternal leucocytes in the mononuclear cell layer and identification of monoclonal antibodies effective in carrying out this separation, which results in production of a maternal sample enriched in fetal nucleated cells.

HLe-1 (Becton-Dickinson Monoclonal center, Mountain View, Calif., catalog #7463) is a monoclonal antibody available as a direct fluorescein isothiocyanate (FITC) conjugate. It recognizes an antigen present on mature human leucocytes and on very immature erythrocyte precursors, but not on mature nucleated erythrocytes (Loken, M. E., et al., *Blood*, 69:255–263 (1987)). Thus, maternal leucocytes are recognized and bound, but fetal nucleated erythrocytes are not, making separation of the two possible. As described in detail in Example 1, this labelled antibody was used to eliminate maternal leucocytes in the mononuclear cell layer.

As is also described (Example 1), a combination of monoclonal antibodies has been used for the same purpose (i.e., elimination of maternal cells from the blood sample). As described, anti-monocyte antibody (M3) and anti-lymphocytes antibody (L4) have been used to remove maternal cells from the mononuclear cell layer resulting from density gradient centrifugation.

Monoclonal antibodies which recognize fetal nucleated cells but do not recognize maternal cells were also identified. As described in detail in Example 1, a monoclonal antibody which recognizes the transferrin receptor was identified. Erythroblasts have been shown to express the transferrin receptor (Loken, M. R., et al., *Blood*, 69:255–263 (1987)) antigen on their cell surfaces from the BFU-E stage until nuclear extrusion (Loken, M. R. et al., *Blood*, 69:255–263 (1987)). The transferrin receptor is also present on activated lymphocytes (Trowbridge, I. S. and M. B. Omary, *Proc. Natl. Acad. Sci. USA*, 78:3039–3043 (1981)), certain tumor cells (Greaves, M. et al., *Int. J. Immunopharmac.*, 3:283–300 (1981)), and trophoblast cells (Galbraith, G. M. P. et al, *Blood*, 55:240–242 (1980)). Thus, such an antibody is specific for or recognizes (binds to) fetal nucleated cells, but not maternal leucocytes. As described in Example 1, commercially available fluorescein-conjugated monoclonal antibodies against the transferrin receptor (TfR) were used to separate fetal nucleated erythrocytes from maternal cells. Although the antibody is not specific for fetal nucleated erythrocytes, it facilitated their enrichment in the flow-sorted samples. Other monoclonal antibodies which are able to distinguish between fetal nucleated cells and maternal cells present in a blood sample can also be used. Such antibodies include commercially available monoclonal antibodies and those which can be produced using known techniques.

Separation of fetal nucleated cells from a maternal blood sample using antibodies described above can be carried out with samples of whole blood or a fraction of whole blood (i.e., one resulting from treatment or processing of whole blood to increase the proportion of fetal nucleated cells present), referred to as an enriched maternal sample. An enriched maternal sample is produced, for example, in a two-step process. The maternal sample is subjected to initial separation on the basis of size, such as by Ficoll-Hypaque density gradient centrifugation. This results in production of a supernatant layer, which contains platelets; a mononuclear cell layer; and an agglutinated pellet which contains non-nucleated erythrocytes and granulocytes. The mononuclear layer is separated from the other layers, to produce a maternal sample which is enriched in fetal nucleated cells.

The maternal sample, whether maternal whole blood or an enriched maternal sample, is subjected to separation, based on surface antigenic differences between fetal nucleated cells and maternal cells using antibodies described above. The maternal sample is contacted with at least one monoclonal antibody which is specific for either fetal nucleated cells or maternal cells, but not for both and, thus, makes it possible to separate the two types of cells. The maternal sample can be combined with a set of two or more monoclonal antibodies, each of which is specific for either fetal or maternal cells, but not for both. The combination of monoclonal antibodies can be designed to enhance separation of the two types of cells (e.g., the combination of anti-TfR antibody and HLe-1 antibody described previously) beyond that possible with a single monoclonal antibody. Separation of the fetal cells is carried out using known techniques, such as flow cytometry, use of immunomagnetic beads and cell panning. In general, the monoclonal antibodies have a detectable label (e.g., radioactive material, fluorophore).

In some cases, fetal nucleated cells persisting from a previous pregnancy may be present in the peripheral blood sample. Steps may be taken to eliminate or significantly reduce the number of such residual nucleated cells if found to be present. Alternatively, a type of fetal nucleated cell known to be associated with the present pregnancy may be selected for detection obviating any potential interference or contamination of the detection method by the residual fetal nucleated cells. For example, fetal nucleated cell type having a relatively short life span may be selected for detection ensuring the fetal nucleated cell is not from a previous pregnancy. Fetal nucleated erythrocytes typically have a life span of about three months in the maternal circulation. The above-identified steps can be conducted using monoclonal antibodies which recognize antigens on the respective cells.

An embodiment of the method of the present invention by which fetal cells are isolated and fetal DNA is detected is represented schematically in FIG. 1. A maternal blood sample (typically 20 ml.) is obtained, using known techniques. The sample is separated into component layers on the basis of size and the mononuclear cell layer, referred to as the maternal sample enriched in nucleated cells (or enriched maternal sample), is removed for further processing. The enriched maternal sample is contacted with at least one monoclonal antibody, as described above, and the resulting fetal nucleated cell/antibody complexes are separated using known methods (e.g., flow cytometry, immunomagnetic beads, cell panning). Fetal DNA is crudely extracted from the resulting complexes (e.g., by heat), thus rendering it available for hybridization with nucleic acid probes. Fetal DNA can be analyzed for a selected DNA sequence or DNA sequences, using known techniques. Prior to analysis, fetal DNA can be amplified, as needed, using known methods (e.g., PCR).

If amplification is to be carried out, the sorted samples are amplified for an appropriate number of cycles of denaturation and annealing (e.g., approximately 24–60). Control samples include a tube without added DNA to monitor for false positive amplification. With proper modification of PCR conditions, more than one separate fetal gene can be amplified simultaneously. This technique, known as "multiplex" amplification, has been used with six sets of primers in the diagnosis of DMD (Chamberlain, J. S., et al., *Prenat. Diagnosis*, 9:349–355 (1989)). When amplification is carried out, the resulting amplification product is a mixture which contains amplified fetal DNA of interest (i.e., the DNA whose occurrence is to be detected and/or quantitated) and other DNA sequences. The amplified fetal DNA of interest and other DNA sequences are separated, using known techniques. Subsequent analysis of amplified DNA can be carried out using known techniques, such as: digestion with restriction endonuclease, ultraviolet light visualization of ethidium bromide stained agarose gels, DNA sequencing, or hybridization with allele specific oligonucleotide probes (Saiki, R. K., et al, *Am. J. Hum. Genet.*, 43 (*Suppl*):A35 (1988)). Such analysis will determine whether polymorphic differences exist between the amplified "maternal" and "fetal" samples. In one embodiment, the amplification mixture is separated on the basis of size and the resulting size-separated fetal DNA is contacted with an appropriate selected DNA probe or probes (DNA sufficiently complementary to the fetal DNA of interest that it hybridizes to the fetal DNA of interest under the conditions used). Generally, the DNA probes are labelled (e.g., with a radioactive material, a fluorophore or other detectable material). After the size-separated fetal DNA and the selected DNA probes have been maintained for sufficient time under appropriate conditions for hybridization of complementary DNA sequences to occur, resulting in production of fetal DNA/DNA probe complexes, detection of the complexes is carried out using known methods. For example, if the probe is labelled, fetal DNA/labelled DNA probe complex is detected and/or quantitated (e.g., by autoradiography, detection of the fluorescent label). The quantity of labelled complex (and, thus, of fetal DNA) can be determined by comparison with a standard curve (i.e., a predetermined relationship between quantity of label detected and a given reading).

The present method has been used to identify Y-specific DNA in nucleated erythrocytes obtained from peripheral blood of pregnant women. This is described in Example 4. Briefly, candidate fetal cells from blood samples obtained from 19 pregnant women were isolated by flow sorting. The DNA in these cells was amplified for a 222 base pair (bp) sequence present on the short arm of the Y chromosome as proof that the cells were derived from the fetus. The amplified DNA was compared with standardized DNA concentrations; 0.1 to 1 ng fetal DNA was obtained in the 20 ml maternal samples. In 7/19 cases, a 222 bp band of amplified DNA was detected, consistent with the presence of male DNA in the isolated cells; 6/7 of these were confirmed as male pregnancies by karyotyping amniocytes. In the case of the female fetus, DNA prepared from cord blood at delivery also showed the presence of the Y chromosomal sequence. In 10/12 cases where the 222 bp band was absent, the fetuses were female. Thus, the Y chromsomal sequence was successfully detected in 75% of the male-bearing pregnancies, demonstrating for the first time that it is possible to isolate fetal gene sequences from maternal blood.

As described in Example 6, male (Y-specific) DNA has been detected in cells sorted from pregnant women at various points in gestation. Briefly, the mononuclear cell layer was isolated from venous blood samples obtained from women between 11 and 16 weeks gestation. Separation was carried out using Ficoll/Hypaque density centrifugation, followed by incubation with monoclonal antibodies (Anti-TfR, anti-Leu 4 and anti-Leu$^M$3) conjugated with a fluorescent marker or compound (fluorescein, phycoerythrin) and dual color analysis and flow sorting on a fluorescence-activated cell sorter. The cells that displayed green fluorescence, but not red fluorescence (TfR positive, Leu negative, Leu M3 negative), were fetal nucleated cells and were separated from the remainder of the sample. These cells were lysed, after which the DNA was amplified and probed for the presence of a 397 bp sequence of the Y chromosome.

Figure 4:
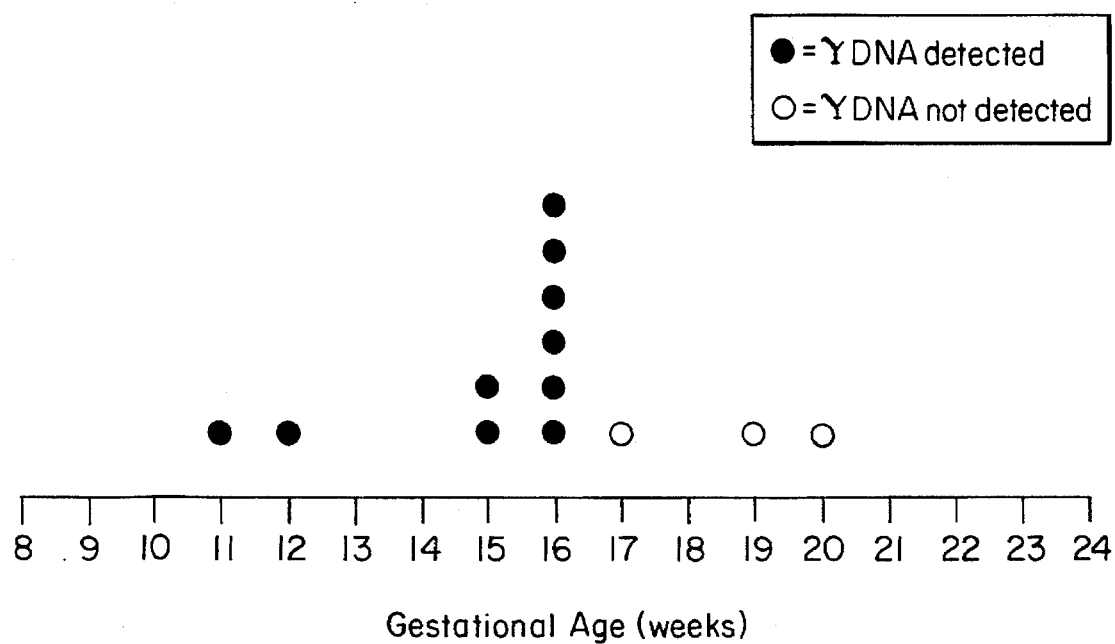
FIG. 4 is a diagram demonstrating the detection of Y chromosomal DNA sequences at various points of gestation in women bearing male pregnancies.
Figure 5A:
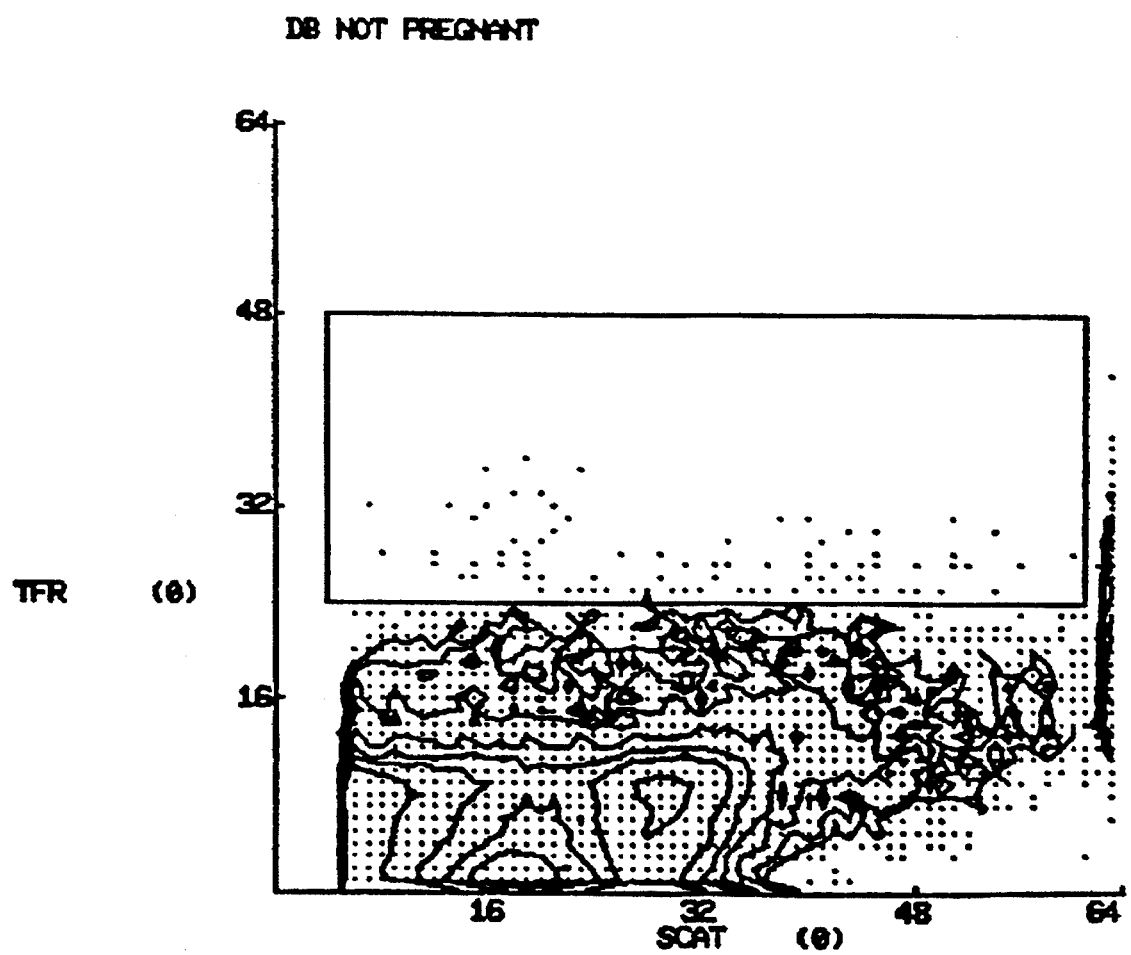
FIGS. 5A, 5B, 5C, 5D, 5E and 5F are a series of histograms obtained when FITC-anti transferrin receptor was used to determine the presence of mononuclear cells in samples from non-pregnant females to which male cells have been added.
Figure 5B:
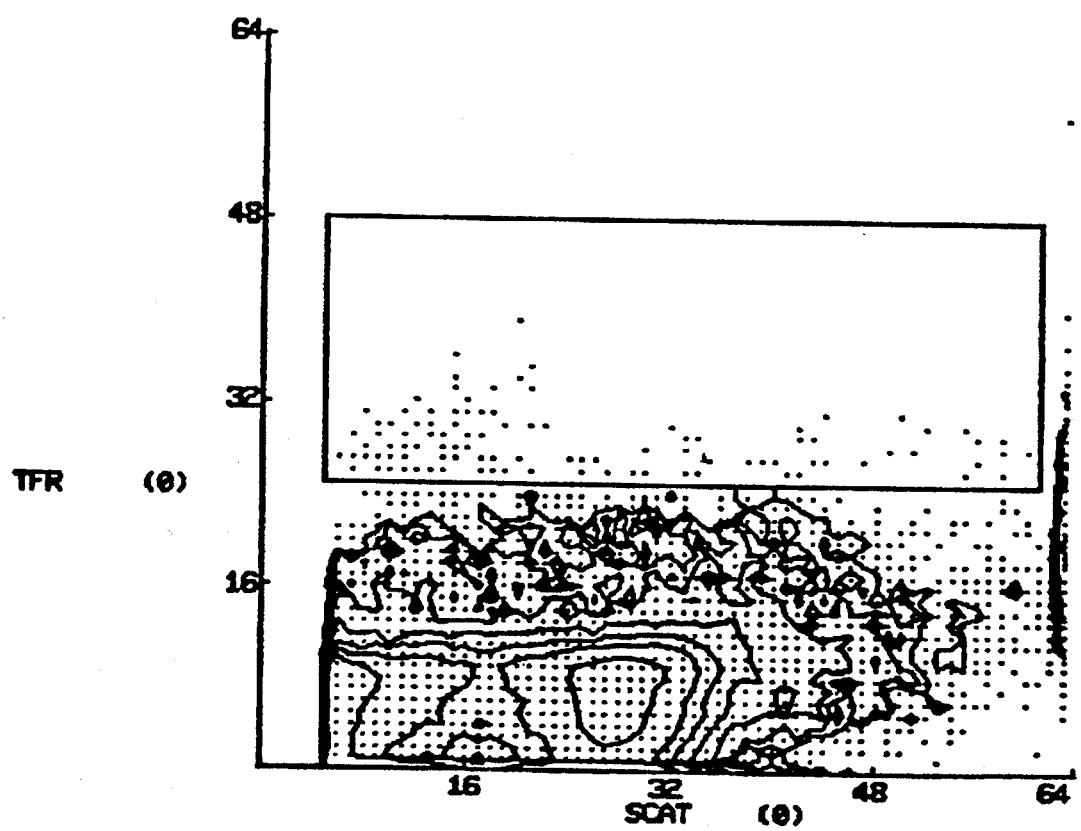
Figure 5C:
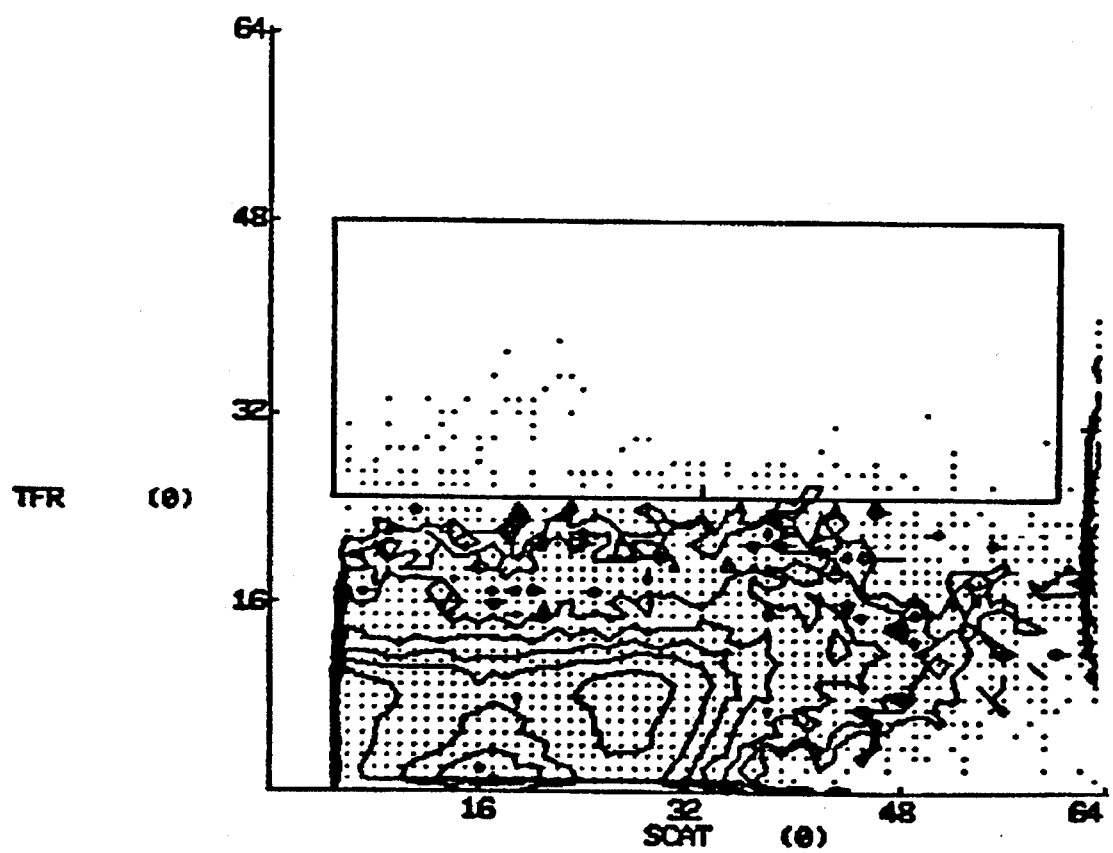
Figure 5D:
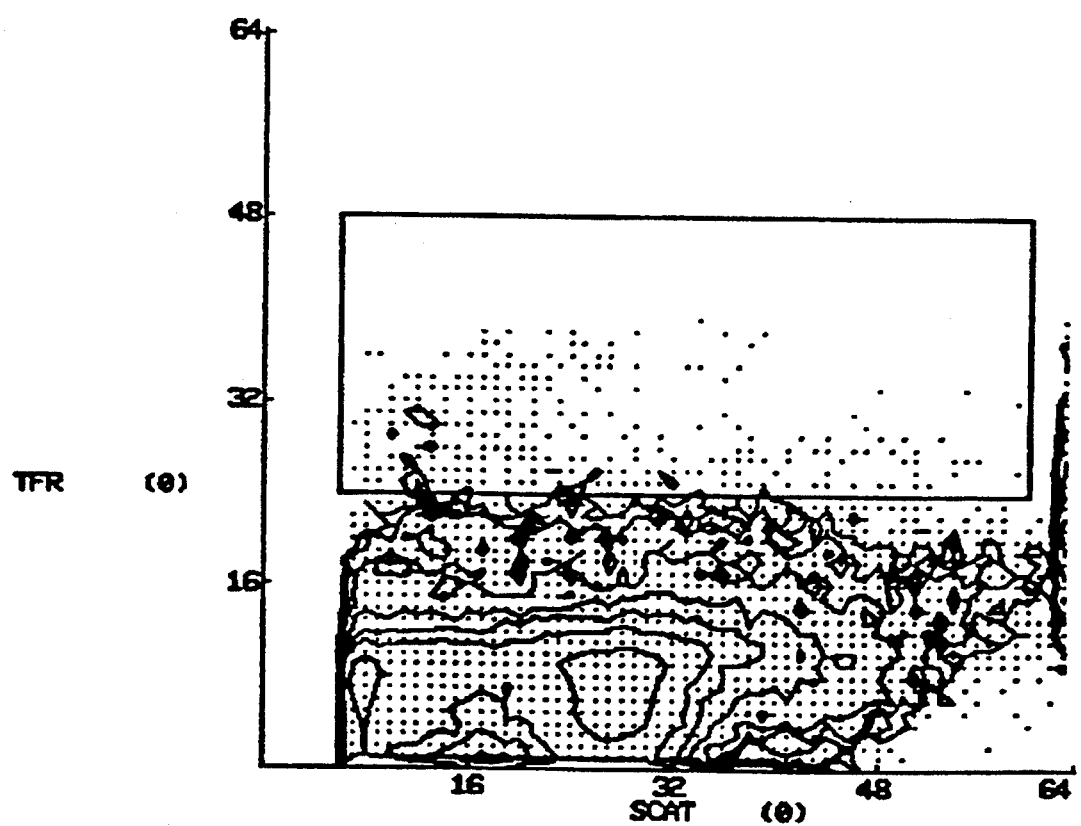
Figure 5E:
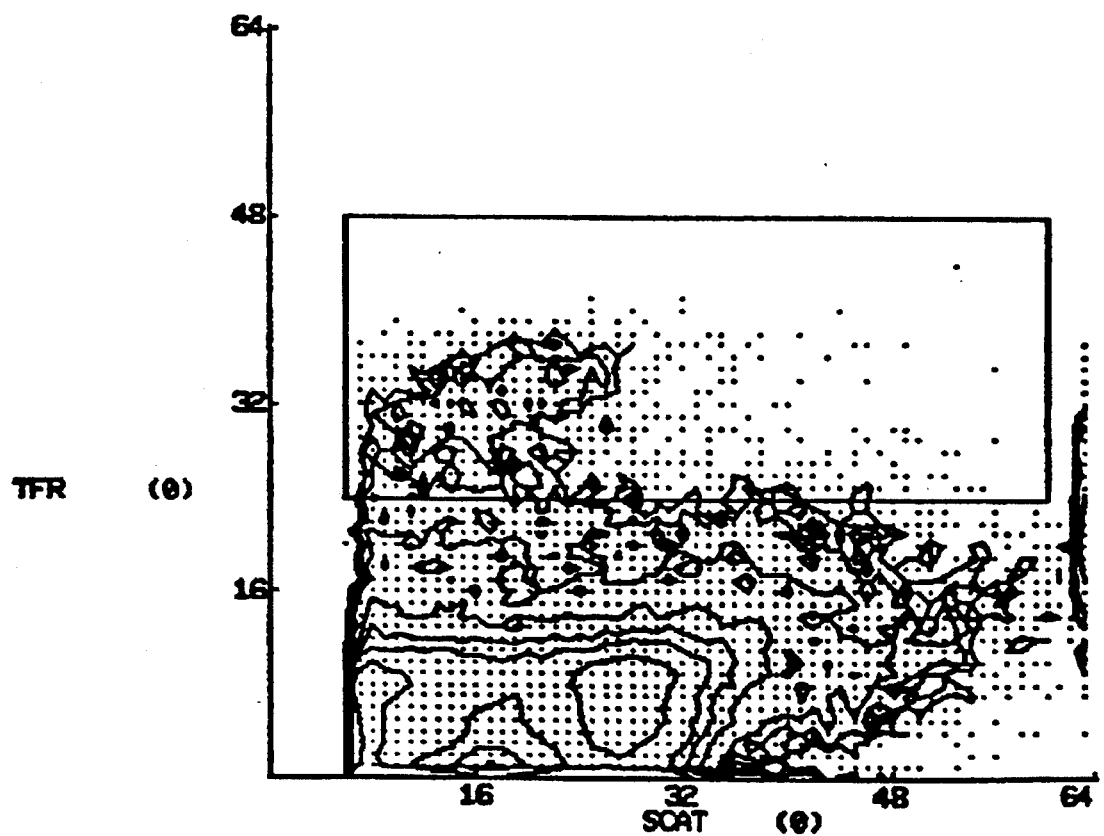
Figure 5F:
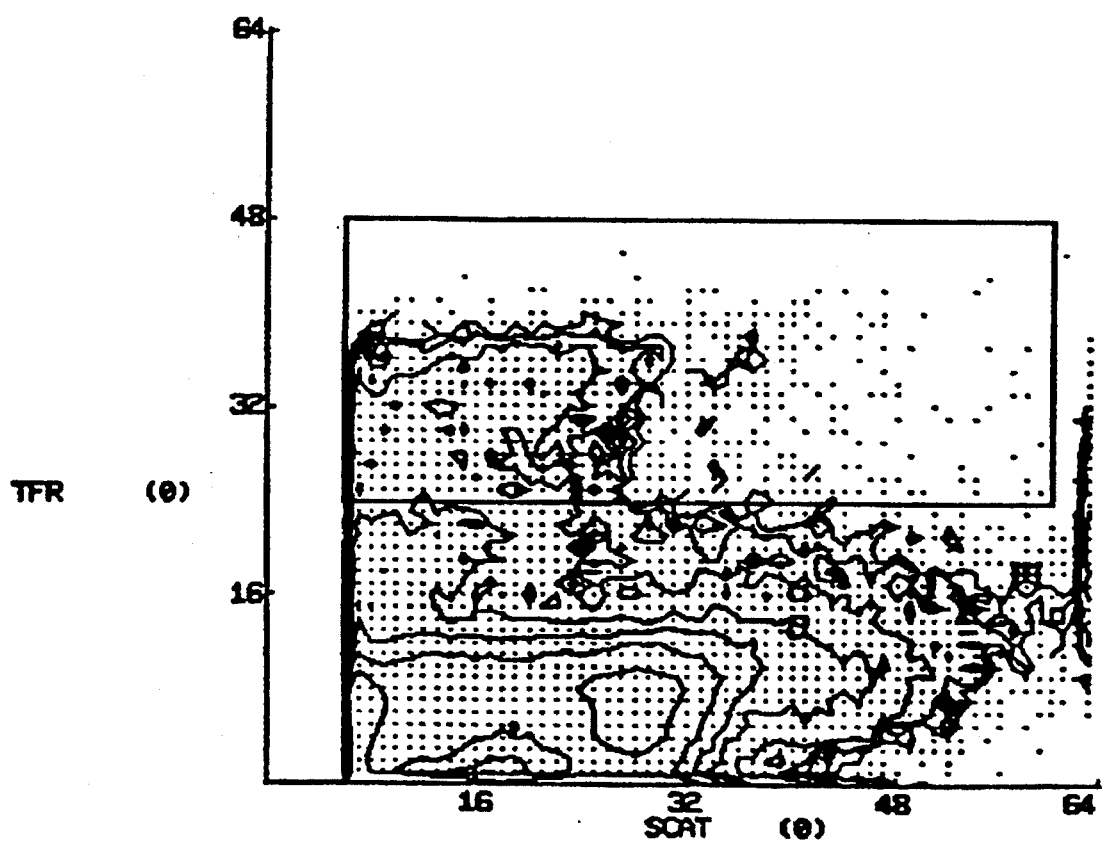

The results presented in Example 6 indicate the procedure allows the detection of the 397 bp sequence present in as little as 5 pg of male DNA. In addition, they suggest that there is a relationship between gestational age and detection of male DNA, as illustrated in FIG. 4. This data suggests there may be a biologic "window" for transfer of fetal nucleated erythrocytes into maternal circulation.

The present method also has been used to distinguish female fetal DNA from maternal DNA. The two types of female DNA were distinguished using amplification of paternal polymorphism, as described in detail in Example 7. Briefly, venous blood samples were collected from women with uncomplicated pregnancies. Separation of fetal nucleated cells was conducted using Ficoll/Hypaque density centrifugation, followed by incubation with monoclonal antibodies (anti-TfR, anti-Leu 4 and anti-Leu M3) conjugated with a fluorescent marker (fluorescein, phycoerthyrin) and dual color analysis and flow sorting on a fluorescence-activated cell sorter. Fetal nucleated cells identified by displaying green fluorescence (TfR positive), but not red fluorescence (Leu-4, Leu-3 negative), were collected and lysed. The DNA from the cells was amplified and probed for paternal sequences of the highly polymorphic region of chromosome 17, which allows the distinction of female fetal DNA from maternal DNA.

The results demonstrated that DNA sequences from the father can be identified in the autosomal chromosomes of the fetus. Consequently, the method of the present invention can be used to separate female fetal nucleated cells, as well as male fetal nucleated cells, from maternal blood. Thus, the method can be used for all DNA-based diagnostic procedures currently being used in other methods, such as amniocentesis.

Further support for the present method's capability to identify Y-specific DNA in nucleated erythrocytes obtained from peripheral blood of pregnant women is given by reconstruction experiments. As described in Example 8, male cord blood was added to blood obtained from non-pregnant females to simulate the presence of fetal cells in maternal blood. Briefly, venous blood samples were collected from healthy, non-pregnant women and the mononuclear cell layers isolated by Ficoll/Hypaque density centrifugation. Mononuclear cells from the umbilical cords of male infants (ranging from $10^2$ to $10^6$ cells) were added to the mononuclear cell layers of the blood of non-pregnant women. The cord blood contains a large percentage of nucleated erythrocytes. The results obtained from these experiments were substantially similar to those obtained from pregnant women at various stages in gestation. Amplified sequences from the Y chromosome, consistent with the presence of male DNA, were detected when $10^2$ male cells were added to the female cells.

Experiments have also indicated that fetal hematopoietic stem cells, as well as nucleated erythrocytes, may be used in the isolation and identification of Y-specific DNA. Example 10 describes the procedure in detail. Briefly, venous blood samples are collected from pregnant women. The mononuclear cell layer is isolated by Ficoll/Hypaque density centrifugation and incubated with monoclonal antibodies which are conjugated with a fluorescent marker and directed against antigens on the surface of hematopoietic progenitor cells (see Example 11 for discussion of antibodies). Fluorescent cells, separated by flow sorting, have bound antibody recognizing primitive cell surface antigens, and thus, are hematopoietic precursor cells. After the cells are lysed by boiling, they are subjected to polymerase chain reaction (PCR) amplification using primers selected to amplify a 397 base pair sequence from the Y chromosome. This method was used to study twenty-five women, eleven of whom have confirmed male pregnancies. In eight of these eleven women (77%), male DNA was detected in sorted cells which showed a positive response to a human progenitor cell antigen, thus, indicating that the cells were undifferentiated hematopoietic stem cells. This experiment confirms that fetal hematopoietic stem cells are circulating in the mother's blood. An additional experiment with an antibody used to detect fetal lymphoblasts (CD10) indicated that in eight of 17 women, male fetal DNA was detected in CD10+ cells. Other antibodies have been identified which recognize human stem cell antigens, as detailed in Example 11. The data demonstrates that the types of fetal cells present vary as the pregnancy proceeds; therefore, it may be desirable to vary the type of antibody used in cell separation, depending on the length of gestation.

As described in Example 12, the present method has been used to analyze venous blood from healthy pregnant women for the presence or absence of Y chromosomal DNA sequences and has been shown to be highly accurate in its ability to do so, as well as to distinguish between samples from women carrying male fetuses and women carrying female fetuses. The only possible source of Y chromosomal DNA in maternal blood is male fetal cells (male cells carrying an X and a Y chromosome and female cells carry two X chromosomes). As described, two antibodies were used, alone or in combination, for this purpose: CD36, which recognizes a cell surface antigen on nucleated erythrocytes and monocytes and glycophorin A, which recognizes an antigen present on erythrocytes. The antibodies were conjugated, directly or indirectly, to a fluorescent dye. Fluorescent cells in the venous sample which bound one or both antibodies were flow sorted and later amplified for Y chromosomal sequences using PCR. Of the 18 women studied, 11 had male fetuses and 7 had female fetuses. Y chromosomal DNA sequences were detected in cells sorted with CD36 and/or glycophorin A antibodies in 10 of the 11 (91%) women with male fetuses and in none of the 7 women bearing females. These results demonstrate that these two antibodies are particularly effective in identifying fetal nucleated cells in maternal blood.

The results of the work described above and in the Examples demonstrate that nucleated fetal cells have been isolated from maternal blood; genomic DNA has been extracted from the fetal cells and identified as being of fetal origin; fetal genes have been amplified using PCR; and selected DNA sequences have been identified in the fetal DNA. It demonstrates for the first time that fetal DNA has been detected in cells isolated from maternal blood.

Uses of the Present Method of Fetal Nucleated Cell Isolation and Fetal DNA Characterization Thus, it has been demonstrated that fetal DNA can be obtained from fetal nucleated cells present in a maternal blood sample. The method of detecting and/or quantitating fetal DNA which is represented in FIG. 1 is useful as a tool for prenatal assessment (e.g., as a means for assessing chromosomal abnormalities, for determining whether DNA associated with a disease is present, or for detecting Y-specific DNA). It is particularly useful because it is noninvasive and requires only a small sample of blood.

Fetal DNA sequences in fetal nucleated erythrocytes, isolated as described herein or by other means by which fetal nucleated cells can be separated from a maternal blood sample, can be analyzed or assessed for the occurrence of a DNA sequence or DNA sequences (gene(s) or gene portion (s)) which are of interest for diagnostic or other purposes. The DNA sequence(s) or gene(s)/gene portion(s) present in fetal cells are referred to herein as fetal DNA of interest. For example, the selected DNA whose presence or absence is to be determined and whose quantity can also be determined is the gene for a disease, such as cystic fibrosis, where the causative gene or gene portion has been cloned and sequenced; alternatively, it is a probe for X- or Y-specific DNA. The same procedure can also be used, with appropriate modifications (e.g., an appropriate DNA probe, time, temperature), to detect other genes or gene portions.

As used in a diagnostic context, such as to detect the gene known to cause cystic fibrosis, the present method is carried out as follows: Initially, a maternal blood sample (typically 20 ml.) is obtained and separated into component layers based on relative weights (e.g., by Ficoll-Hypaque density gradient centrifugation) to remove non-nucleated erythrocytes and produce a mononuclear cell layer. This results in production of a maternal blood sample enriched in fetal nucleated erythrocytes. The mononuclear cell layer is stained with at least one appropriate monoclonal antibody (e.g., one which is specific for the type of fetal nucleated cell to be separated from the sample). For example, a monoclonal antibody specific for fetal nucleated cells, such as anti-TfR antibody, described above, can be used. In general, the monoclonal antibody used bears a detectable label. Alternatively, a combination of selected labelled monoclonal antibodies, such as monoclonal antibodies specific for fetal nucleated cells (e.g., anti-TfR antibody) and monoclonal antibodies specific for maternal leucocytes (Hle-1 or L4 and M3), each labelled with a different fluorescent compound, can be used to remove essentially all maternal cells. Labelled cells are subsequently separated from one another using a known method, such as flow cytometry. Binding of the monoclonal antibodies to cells for which they are specific results in production of labelled monoclonal antibody-cell complexes. For example, in the case in which anti-TfR antibodies and HLe-1 are used, fetal nucleated erythrocytes are bound by anti-TfR antibody, to produce fetal nucleated erythrocytes/anti-TfR antibody complexes, and maternal leucocytes are bound by HLe-1 antibody complexes. The fetal nucleated erythrocyte/anti-TfR antibody complexes are separated from maternal cell/HLe-1 antibody complexes, using, for example, flow cytometry. The fetal cells are lysed, to produce crudely extracted fetal DNA which is subsequently amplified, using, for example, PCR. This results in production of amplified fetal DNA, which is subsequently separated on the basis of size. Size-separated fetal DNA is contacted with labelled DNA probes (i.e., in prenatal detection of cystic fibrosis, a labelled DNA probe complementary to the gene associated with cystic fibrosis). If the fetal DNA contains DNA of interest (in this case, the gene associated with cystic fibrosis), fetal DNA of interest/labelled probe complexes are formed.

Fetal DNA of interest/labelled probe complexes are subsequently detected, using a known technique, such as autoradiography. Simple presence or absence of labelled fetal DNA of interest can be determined or the quantity of fetal DNA of interest can be determined. In either case, the result is assessment of fetal DNA obtained from a maternal blood sample for selected DNA.

The occurrence of fetal DNA associated with diseases or conditions other than cystic fibrosis can also be detected and/or quantitated by the present method. In each case, an appropriate probe is used to detect the sequence of interest. For example, sequences from probes St14 (Oberle, I., et al., *New Engl. J. Med.*, 312:682–686 (1985)), 49a (Guerin, P., et al., *Nucleic Acids Res.*, 16:7759 (1988)), KM-19 (Gasparini, P., et al., *Prenat. Diagnosis*, 9:349–355 (1989)), or the deletion-prone exons for the Duchenne muscular dystrophy (DMD) gene (Chamberlain, J. S., et al., *Nucleic Acids Res.*, 16:11141–11156 (1988)) are used as probes. St14 is a highly polymorphic sequence isolated from the long arm of the X chromosome that has potential usefulness in distinguishing female DNA from maternal DNA. It maps near the gene for Factor VIII:C and, thus, may also be utilized for prenatal diagnosis of Hemophilia A. Primers corresponding to sequences flanking the six most commonly deleted exons in the DMD gene, which have been successfully used to diagnose DMD by PCR, can also be used (Chamberlain, J. S. et al., *Nucleic Acids Res.*, 16:11141–11156 (1988)). Other conditions which can be diagnosed by the present method include β-thalassemia (Cai, S-P., et.al., *Blood*, 73:372–374 (1989); Cai, S-P., et al., *Am. J. Hum. Genet.*, 45:112–114 (1989); Saiki, R. K., et al., *New Engl. J. Med.*, 319:537–541 (1988)), sickle cell anemia (Saiki, R. K., et al., *New Engl. J. Med.*, 319:537–541 (1988)), phenylketonuria (DiLella, A. G., et al., *Lancet*, 1:497–499 (1988)) and Gaucher disease (Theophilus, B., et al., *Am J. Hum. Genet.*, 45:212–215 (1989)). An appropriate probe (or probes) is available for use in the present method for assessing each condition.

It is also possible to separate fetal cells from maternal cells by means other than flow cytometry, as mentioned previously, and to analyze fetal nucleated erythrocyte DNA obtained in this way. Such separation procedures may be used in conjunction with or independent of flow cytometry. This is advantageous because lack of access to a flow cytometer, as well as expense, could limit potential applications of this technique. Thus, other methods of fetal cell separation can be used. The separation method used can result in elimination of unwanted cells ("negative selection") or isolation of rare but desirable cells ("positive selection").

In one embodiment, the maternal cells are depleted prior to fetal cell sorting. The mononuclear cell layer is initially isolated from the blood of pregnant women by Ficoll-Hypaque centrifugation. The resulting cell suspension consists predominantly of maternal cells; in order to enrich the eventual proportion of fetal cells present, the maternal cells are selectively removed by incubating the cells with antibodies attached to a solid support. Such supports include magnetic beads, plastic flasks, plastic dishes and columns. The antibodies bind antigens present on the cell surface of mature leukocytes. Thus, the majority of maternal leukocytes are eliminated by virtue of being bound to the solid support. The total number of cells remaining in the cell suspension is smaller, but the proportion of fetal cells present is larger.

Separation by immunomagnetic beads or by cell panning can also be used. In this embodiment, the mononuclear cell layer is isolated, as described previously. This layer is then mixed with antibody-coated polymer particles containing magnetic cores (e.g., "Dynabeads"). These immunomagnetic beads are available coated with a variety of antibodies. For example, immunomagnetic beads coated with antibody to leucocyte antigens and antibody to mouse immunoglobulins, which can be subsequently conjugated to mouse monoclonal antibody against the human transferrin receptor, can be used. After mixing, the rosetted cells are isolated with a magnetic particle concentrator. In one embodiment, two sets of antibody-coated immunomagnetic beads are used in succession. First, the maternal leucocytes are depleted and then the remaining TfR positive cells are collected. Subsequent steps in the method (amplification, separation, contact with an appropriate DNA probe or probe set) are as described for cells separated by flow cytometry.

Mueller et al. (*Lancet*, 336:197–200 (1990)) have described a method of isolating placenta-derived trophoblast cells in the blood of pregnant women using magnetic beads. This method included mixing 1 ml of monoclonal antibody hybridoma culture supernatant with $2 \times 10^7$ magnetic beads precoated with sheep antibody to mouse IgG (Fc fragment) (Dynabeads M-450, Dynal AS, Oslo, Norway), and incubated overnight at room temperature. The coated beads were stored at 4° C. and washed three times in ice-cold RPMI 1640 medium containing lithium heparin (10 IU/ml). The blood from the pregnant women was collected into tubes containing 10 IU of lithium perml of whole blood, diluted 1:10 with RPMI containing lithium, and incubated with the antibody coated beads at 4° C. overnight. The desired cells were bound to the antibody on the bead; the beads collected by means of a cobalt-samarium magnet. Although in this case the antibody was directed against trophoblast antigens a similar technique can be utilized with, for example, antibody to cell surface antigens present on fetal nucleated erythrocytes and not present on maternal cells. An advantage to this particular technique is that an initial step which results in mononuclear cell isolation is not added. Additionally, the magnetic beads can be used for both positive (fetal cells) and negative (maternal cells) selection.

An alternative method of isolation can be a modification of the method described by R. J. Berenson et al. (*J. of Immunol. Methods*, 91(1986)) in which the high affinity between the protein avidin and the vitamin biotin was exploited to create an indirect immuno-adsorptive procedure. In this technique, avidin was linked to cyanogen bromide activated sepahrose 6 MB beads and washed in an alternating fashion with coupling buffer (0.1M $NaHCO_3$ in 0.5M NaCl at pH 8.3). and washing buffer (0.1M sodium acetate in 0.5M NaCl at pH 4.5) and stored at 4° C. The blood cells were incubated with 1) murine monoclonal antibody, and 2) biotinylated goat anti-mouse immunoglobulin. A 3 ml column of gel was packed in Pharmacia K 19/15 column. The treated cells were passed through the column in phosphate buffered saline containing 2% bovine serum albumin. Adherent cells were dislodged by mechanical agitation. This technique can be applied to fetal cell separation if the antibodies used recognize fetal cell surface antigens or maternal cell surface antigens, but not both. Variation in methods for conjugating antibodies to beads exist; examples include those described by Thomas and co-workers (Thomas, T. E., et al. (*J. of Immuno Methods*, 120:221–131 (1989)) and by deKretser and co-workers (deKretser, T. A., et al. (*Tissue Antigens*, 16:317–325 (1980))). The use of an antibody-bound column does not require the preliminary isolation of the mononuclear cell fraction from whole blood.

Another alternative to mononuclear cell isolation is to selectively lyse maternal non-nucleated erythrocytes. A number of buffers, including 0.17M $NH_4Cl$, 0.01M Tris, pH 7.3, have been described in the literature and are well known in isolation of hematopoietic stem cells for bone marrow transplantation. Other buffers ("Lyse and Fix", GenTrak) are available commercially.

Once the fetal cells are isolated from maternal blood, they may be cultured to increase the numbers of cells available for diagnosis, if desired. E. Fibach et al. (*Blood*, 73:100–103 (1989)) have described a method that supports the growth of human hematopoietic progenitor cells. This step-wise method involves 1) initial culture in the presence of conditioned medium from human bladder carcinoma cells, 2) removal of leucocytes by harvest of non-adherent cells and lysis with monoclonal antibodies and 3) reculture of cells in medium supplemented by recombinant erythropoietin.

Other methods of separating fetal nucleated cells from maternal cells can also be used, provided that they make it possible to differentiate between fetal cells and maternal cells, and to isolate one from the other.

A kit for use in carrying out the present method of isolating and detecting fetal DNA of interest, such as a chromosomal abnormality associated with a disease or other condition, in a maternal blood sample can be produced. It includes, for example, a container for holding the reagents needed; the reagents and, optionally, a solid support for use in separating fetal nucleated cell/specific antibody complexes from other sample components or for removing maternal cells complexed with a specific antibody. For example, reagents in a kit to be used in detecting fetal DNA of interest after amplification of fetal DNA by PCR can include: 1) at least one antibody specific for a surface antigen characteristic of fetal nucleated cells but not specific for a surface antigen characteristic of maternal leucocytes; selected DNA primers for use in amplifying fetal DNA by PCR; and at least one DNA probe complementary to the fetal DNA to be detected (fetal DNA of interest). The kit, as indicated, can also include a solid support to be used in separating complexes formed from other samples components. Such solid support can be, for example, a glass slide, nitrocellulose filter, or immunomagnetic beads and can have affixed thereto an antibody selective for the antibody present in the fetal nucleated cell/specific antibody complexes.

The present invention will now be illustrated by the following examples, which are not intended to be limiting in any way.

EXAMPLE 1

Antibody Selection for Isolation and Sorting of Fetal Nucleated Erythrocytes (NRBCs)

Removal of Maternal Leucocytes from Maternal Blood using Human Leucocyte Antigen (HLe-1)

The technique of fetal NRBC isolation began with an initial Ficoll-Hypaque density gradient centrifugation to remove the tremendously high number of non-nucleated erythrocytes in maternal blood. Peripheral blood was centrifuged and separated into a supernatant layer containing platelets, a mononuclear cell layer, and an agglutinated pellet consisting of non-nucleated erythrocytes and granulocytes. The mononuclear cell layer consisted of lymphocytes, monocytes, possible trophoblasts, and, due to their increased size and density, NRBCs and some reticulocytes. While the Ficoll-Hypaque centrifugation represented an initial enrichment in the proportion of fetal NRBCs present in the maternal sample, flow cytometry and cell sorting was used to improve the purity of the isolated cell population.

The mononuclear cell layer from peripheral blood samples in 63 pregnant women, 15 nonpregnant adults, and 39 umbilical cords, was stained with FITC-HLe-1 for flow cytometric analysis. Umbilical cord samples were used as a substitute for whole fetal blood. Representative histograms displaying fluorescence versus low-angle light scatter (an approximation of cell size) for each of the three groups were generated. Histogram peaks were identified that corresponded to leucocytes, erythrocytes and platelets. In 9 pregnant women, 7 nonpregnant adults and 12 umbilical cord samples, fluorescent (HLe-1 positive) and non-fluorescent (HLe-1 NEGATIVE) cell populations were sorted for detailed microscopy after Wright-Giemsh staining. While the HLe-1 positive populations were always composed of leucocytes independent of the sample source, the HLe-1 negative populations differed.

In cord blood, the HLe-1 negative cells were nonnucleated and nucleated erythrocytes with occasional platelets. In the pregnant women, there were platelets, non-nucleated erythrocytes, and a very rare NRBC. In non-pregnant adults, only platelets and debris were seen. Thus, cord blood, with it high percentage of NRBCS, was used as a reference to establish cell sorting parameters. Microscopy confirmed the specificity of the antibody-antigen binding and that the sorted HLe-1 negative cells were relatively free from leucocyte contamination. These sorting parameters were utilized to isolate potential fetal NRBC on 40 pregnancies.
Enrichment of Fetal NRBC in Maternal Blood using Transferrin Receptor Antigen (TfR)

The transferrin receptor (Newman, R., et al., Trends Biochem. Sci. 1:397–399 (1982)) is a surface glycoprotein important in cellular iron transport. The TfR is present on activated lymphocytes (Trowbridge, I. S., et al., Proc. Natl. Acad. Sci. USA, 78:3039–3043 (1981)), certain tumor cells (Greaves, M. et al., Int. J. Immunopharmac., 3:283–300 (1981)), and trophoblast cells (Galbraith, G. M. P., et al., Blood, 55:240–242 (1980)). Erythroblasts express the TfR on their cell surfaces from the BFU-E stage until nuclear extrusion (Loken, M. R., et al., Blood, 69:255–263 (1987)). Thus, TfR is an excellent "candidate antigen" for enrichment of fetal NRBCs found in maternal blood. Monoclonal antibody against TfR is available as both a fluorescein conjugate (Becton-Dickinson catalog #7513) and a phycoerythrin (PR) conjugate (gift of Dr. Michael Loken, Becton-Dickinson). The mononuclear cell layer was isolated from peripheral blood samples in 6 pregnant women, 4 non-pregnant adults, and 3 newborn umbilical cords for TfR analysis and microscopy. Representative histograms of fluorescence versus light scatter from these three groups were generated.

Whereas umbilical cord samples had a large population of fluorescent TfR positive cells) that were heterogenous in size, non-pregnant adults and pregnant adults had smaller percentages of fluorescent cells that clustered in discrete groups. In addition, there were slight differences in the percentages of TfR positive cells in the pregnant (mean= 0.83) versus non-pregnant (mean=0.32) samples studies.

Microscope studies of the TfR positive cells were performed using Wright-Giemsa stain for morphology and Kleihauer-Betke technique for the detection of fetal hemoglobin (Kleihauer, E., et al., Klin Wochenschr., 35:637–638 (1957)). In the umbilical cord samples, large numbers of nucleated and non-nucleated erythrocytes containing fetal hemoglobin and occasional leucocytes were identified visually. In the pregnant women, the predominant cell types were nucleated and non-nucleated erythrocytes containing fetal hemoglobin, although leucocytes were infrequently observed. In contrast, the samples from the non-pregnant controls consisted almost exclusively of lymphocytes and monocytes. Because trophoblast cells express TfR, it was postulated that they might be present in the sorted population from the pregnant women; none was detected.
Dual Antibody Analysis Because both antibodies enriched the proportion of NRBCs present, but did not completely exclude other cell types in the sorted samples, combinations of antibodies were used to isolate pure populations of fetal NRBCs. Preliminary dual antibody studies were performed using PE-conjugated TfR and FITC-conjugated HLe-1. NRBCs are TfR positive and HLe-1 negative, whereas maternal leucocytes are HLe-1 positive. These experiments worked well and resulted in separation of maternal leucocytes.

Thus, the work described above defined flow cytometric parameters for enrichment and sorting of NRBCs in peripheral blood from pregnant women. In addition, microscopic studies revealed that morphologic differences occur in mononuclear cell populations derived from venous blood samples in pregnant versus non-pregnant adults.

EXAMPLE 2

DNA Hybridization Studies in HLe-1 Negative Cells Sorted from Maternal Blood

To confirm fetal origin of the cells sorted as described in Example 1, Y chromosomal probes were used because it is the Y chromosome that is unquestionably fetal in origin. The assessments were designed to study whether the presence of Y chromosomal DNA in maternal blood as detected on autoradiographs performed antenatally correlated with the subsequent birth of a male infant.
DNA Isolation HLe-1 negative cells from cord blood and pregnant women were sorted into test tubes. Conventional methods of DNA isolation as well as modification of cruder methods (Lau, Y-F, et al. Lancet, 1:14–16 (1984); McCabe, E. R. B., et al., Hum Genet., 75:213–216 (1987) were attempted without success in detecting Y chromosome derived bands on Southern Blots. All were limited by the small numbers of cells present.

EXAMPLE 3

Direct Hybridization to Cells Deposited on Filters

In order to circumvent technical problems associated wtih DNA isolation, a method of direct DNA hybridization to cells flow sorted onto nitrocellulose filters was developed (Bianchi, D. W., et al., Cytometry, 8:197–202 (1987)). In control experiments, the sex of a newborn was determined from as few as 50 sorted cord blood leucocytes or 5,000 HLe-1 negative cells (a mixture of nucleated and non-nucleated cells).

The methodology was then applied to detection of Y chromosomal sequences in HLe-1 negative cells sorted from peripheral blood samples in 40 women between 8½ and 38 weeks gestation. Results were the following:

| Dot Blot Hybridization with Y Chromosomal Probe | Delivered Male Infant | Delivered Female Infant | Lost To Follow-up |
|---|---|---|---|
| + | 3 | 2 | 0 |
| − | 21 | 12 | 2 |

It was concluded that hybridization with this probe was not predictive of male pregnancy. The possibility exists that there was fetal DNA present on the filters where DNA hybridization occurred, but that this DNA bound to the Y probe nonspecifically. Thus, the filters interpreted as "positive" for male DNA might actually have been "positive" for fetomaternal hemorrhage.

EXAMPLE 4

Use of the Polymerase Chain Reaction (PCR) to Amplify Gene Sequences in Sorted Fetal Cells PCR, which has a capacity for making $10^6$ copies of rare target gene sequences, was used to amplify gene sequences in sorted fetal cells. Optimum conditions for PCR, given the minute amounts of DNA expected after a fetal cell sort (approximately 1 pg to 100 ng), were determined. Experimental conditions were modified as new information became available. For example, Taq polymerase was used instead of Klenow fragment of *E. Coli* DNA polymerase (Kogan, S. C. et al., *New England J. Med.* 317:990 (1987)) because of its increased specificity in DNA replication.

Initially, studies were performed on repeated sequences from the long arm of the Y chromosome, probe Y431-Hinfa (given by Dr. Kirby Smith, Johns Hopkins University, Baltimore, Md.) and the short arm of the Y chromosome, probe Y411 (Given by Dr. Ulrich Muller, Children's Hospital, Boston, Mass.). Repeated sequences were selected because they would create a stronger amplification signal from a rare male fetal cell. Y411 is identical to Y156 (Muller, U., et al., *Nucleic Acids Res.*, 14:1325–1329 (1986)), is repeated 10–60 fold, and is absolutely Y specific on Southern blots. Sequence Y431 has autosomal homology in females that limited its usefulness in sex determination.

PCR Standardization

To define the minimum amount of DNA detectable in maternal blood, a series of standardization experiments were done. DNA from male and female individuals was prepared in tenfold dilutions (1 pg to 1 mcg) and amplified using the standard reagents in the GeneAmpkit (Perkin-Elmer Cetus cat #N801-0055) on a Perkin-Elmer DNA Thermal Cycler. Primers 411-01 and 411-03 were designed to amplify a 222 base pair (bp) sequence within probe Y411. The number of amplification cycles varied between 18 and 30. Amplified DNA samples were electrophoresed on agarose gels, transferred to nylon filters, and hybridized to $^{32}$P-labeled Y411 probe. While it appeared possible to detect Y specific bands on autoradiographs in lanes containing as little as 10 pg of male DNA, results were often muddled by the presence of amplified DNA in female lanes or control lanes containing no added DNA. The phenomenon of "false positive amplification" has now received universal recognition (Lo, Y-M.D., et al., *Lancet*, 2:697 (1988); Kwok, S., et al, *Nature*, 339:237–238 (1989)).

Elimination of "False Positive" Amplification

Due to the limited amount of starting material in a fetal cell sort, every effort was made to eliminate background amplification in order to determine which fetuses truly possess Y chromosomal DNA. Thus, measures were taken to prevent aerosol contamination of male DNA. All PCRs were performed under sterile conditions, wearing gloves, and using positive displacement pipettes. All reagents were prepared in a sterile manner and incubated overnight prior to PCR with a restriction endonuclease having a digestion site within the target sequence. These precautions resulted in a significant decrease and virtual absence of false positive amplification, as monitored by running control reactions with all reagents but no DNA.

Successful Isolation and Amplification of Fetal Gene Sequences from NRBCs in Maternal Blood After eliminating sources of DNA contamination and determining that as little as 10 pg of male DNA (1 cell 7 pg of DNA) could be detected after PCR amplification, candidate fetal cells from the peripheral blood of 19 women at 12½ to 17 weeks gestation were sorted. Monoclonal antibody against TfR was used to identify the presumed NRBC. The DNA in the sorted cells was amplified for the 222 bp sequence in probe Y411 as proof that the cells were derived from the fetus in male pregnancies. In 7/19 cases the 222 bp band of amplified DNA was detected on autoradiographs, consistent with the presence of male DNA in the isolated cells; 6/7 of these were confirmed as male pregnancies by karyotyping amniocytes. In the case of one female fetus, repeat studies at 32 weeks gestation and cord blood at delivery also showed the presence of the Y chromosomal sequence. This result might be explained by a low level of sex chromosome mosaicism, XX/XY chimerism (Farber, C. M., et al., *Hum. Genet.*, 82:197–198 (1989)), or the presence of the Y411 sequence in single copy on the X chromosome or autosomes. In 10/12 cases where the 222 bp was absent, the fetuses were female. Therefore, detection of the Y chromosomal sequence was successful in 6/8 of 75% of the male-bearing pregnancies. In the two pregnancies where male DNA was not detected, there may have been fetomaternal blood group incompatibility. Alternatively, there may not have been fetomaternal hemorrhage or the number of NRBCs present may have been below the limit of sensitivity for detection of DNA. The conditions used made it possible to detect a minimum of 100 pg of fetal DNA, or the equivalent of 15 fetal cells. The limit of sensitivity can be improved by extending the number of cycles used in PCR. This work demonstrated that for the first time, fetal DNA was detected in cells isolated from maternal blood.

To further decrease false positive amplification and permit detection of fetal DNA at the single cell level on agarose gels, PCR is being carried out using primers derived from a single copy of sequence specific for the long arm of the Y chromosome, PY49a (Guerin, P., et al., *Nucleic Acids Res.*, 16:7759 (1988)). In preliminary experiments using 60 cycles of PCR, Y chromosomal DNA is visible on ethidium-bromide stained agarose gels. This extraordinary degree of sensitivity will now be applied to DNA from sorted fetal cells.

EXAMPLE 5

Determination of the Volume, Morphology and Universality of Fetomaternal Hemorrhage a. General Strategy It is also possible, because of the availability of the present method of isolating fetal nucleated cells from blood obtained from a pregnant woman, to determine whether fetal cells can be found in the maternal blood in all pregnancies. A data base can be created that can provide information on the number and type of fetal cells circulating in maternal blood as pregnancy progresses. Based on previous work, it is anticipated that there will be a normal range of values that is dependent on gestational age; deviation from these values will be studied as a potential indication of a pregnancy at risk. Specifically, large amounts of fetal blood in the maternal circulation may be correlated with placental abnormalities, threatened miscarriage and intrauterine growth retardation.

Maternal venous blood samples are collected from pregnant women, generally prior to any invasive procedures. In general, a single 20 ml. venous blood sample will be obtained. In a subgroup of patients, permission will be sought to draw blood samples every 4 weeks to follow changes in numbers of fetal cells present. Blood is collected in EDTA, diluted 1:1 with Hanks Balanced Salt Solution (HBSS), layered over a Ficoll-Hypaque column (Pharmacia) and spun at 1400 rpm for 40 minutes at room temperature. The mononuclear cell layer will be isolated, washed twice with HBSS and stained with fluorescent monoclonal antibodies. For example, this can be a combination of fluorescein isothiocyanate-conjugated antitransferrin receptor (TfR) and phycoerythrin-conjugated anti-monocyte antibodies (M3, Becton-Dickinson catalog 17497) and anti-lymphocyte antibodies (L4, Becton Dickinson catalog #7347). The staining occurs on ice, in phosphate buffered saline (PBS) containing 2% fetal calf serum and 0.1% sodium azide. The cells are washed in PBS prior to flow cytometry. Analysis and sorting are performed on a Becton-Dickinson FACS-IV interfaced with a Consort 40 program. Data will be acquired on the relative size and fluorescence (in two colors) of the analyzed cells. Cells that are fluorescent in the green wavelength (TfR positive) and not fluorescent in the red wavelength (L4 and M3 negative) will contain the presumed fetal NRBCs. The percentage of these cells in the mononuclear cell layer are recorded and analyzed as a function of gestational age. These cells are sorted for microscopy and PCR amplification. In addition, cells that are not fluorescent in the green wavelength (TfR negative) but are fluorescent in the red wavelength (L4 and/or M3 positive) are sorted as a presumed maternal leucocyte population and source of maternal DNA polymorphisms.

An additional benefit of studying nucleated fetal cells in maternal blood is that the amount of fetal DNA present can be extrapolated to determine the extent of fetomaternal hemorrhage in normal and unusual pregnancies. In the pregnancies studied, an average amount of 1 ng of fetal DNA (corresponding to 150 NRBCs) was present. Using published values of the number of NRBCs per liter of fetal blood at 16 weeks, (3.6×10$^9$) (Millar, D. S. et al., Prenat. Diagnosis, 5:367–373 (1985); (Forestier, F., et al., Pediatr. Res., 20:342–346 (1986)) and doing simple algebra, these results were calculated to be consistent with 2–20 µl hemorrhage of fetal blood into maternal circulation. This is a trivial amount when compared with the fetoplacental blood volume at 16 weeks, about 20 ml. It is important to validate and extend these results to generate normative data regarding fetomaternal transfusion in early pregnancies. It will be equally important to correlate deviations from the expected results with pregnancy complications.

EXAMPLE 6

Detection of Male DNA in Cells Sorted from Pregnant Women at Different Points in Gestation Venous blood samples (20 ml) were collected in EDTA from healthy women with uncomplicated pregnancies, prior to invasive diagnostic procedures, at different points in gestation. The mononuclear cell layer was isolated by Ficoll/Hypaque density centrifugation and incubated with the monoclonal antibodies fluorescein (FITC)-conjugated anti-TfR, phycoerythrin (PE)-conjugated anti-Leu 4 and PE-conjugated anti-Leu M3 (Becton-Dickinson). Dual color analysis and flow sorting were performed on a fluorescence-activated cell sorter.

Cells that display green fluorescence but not red fluorescence (TfR positive, Leu 4 negative, Leu M3 negative) were collected into sterile micro test tubes and frozen at −20° C. Prior to polymerase chain reaction amplification, the cells were lysed by boiling. The polymerase chain reaction (PCR) was performed under standard conditions using standard reagents as described in Example 4. The primers used to amplify material from the Y chromosome define a 397 base pair (bp) sequence. After PCR, the patient samples were analyzed with conventional Southern blots using $^{32}$P labelled probe. Ethidium bromide stained agarose gels and autoradiographs were examined for the presence of the 397 bp band, which is considered significant only if reagent controls do not reveal false positive amplification.

Under the reaction conditions described above, it was possible to detect the 397 bp male specific band if 5 pg of male DNA was present. This is approximately the amount of DNA present in one cell. When excess female DNA (500 ng) was added to the reaction mixture, the male specific band was consistently detectable at 100 pg.

FIG. 4 represents a summation of samples obtained from twelve women bearing male fetuses. These samples were taken at different times in pregnancy, and one woman was sampled twice. The data indicates that there is a relationship betwen gestational age and the detection of male DNA. This implies a potential biologic "window" for the transfer of fetal nucleated erythrocytes into the maternal circulation.

EXAMPLE 7

Detection of Female Fetal DNA by Amplification of Paternal Polymorphisms

Venous blood samples (20 ml) were collected in EDTA from health women with uncomplicated pregnancies. The mononuclear cell layer was isolated by Ficoll/Hypaque density centrifugation and incubated with the monoclonal antibodies fluorescein (FITC)-conjugated anti-TfR, phycoerythrin (PE)-conjugated anti-Leu 4 and PE-conjugated anti-Leu M3 (Becton-Dickinson). Dual color analysis and flow sorting were performed on a fluorescence-activated cell sorter.

Cells that display green fluorescence but not red fluorescence (TfR positive, Leu 4 negative, Leu M3 negative) were collected into sterile micro test tubes and frozen at −20° C. Additionally, cells that displayed red fluorescence but not green fluorescence (TfR negative, Leu 4 positive, Leu M3 positive) were collected in an identical manner. Prior to polymerase chain reaction (PCR) amplification, the cells were lysed by boiling. PCR was performed using buffers containing 1 mM MgC$^l$2. The primers used in PCR amplify a highly polymorphic region of chromosome 17. Amplified DNA sequences correspond to blocks of genes transmitted directly from parent to child. As a result of the high degree of individual variation in these sequences, it is uncommon for two parents to manifest identical DNA patterns. Thus, it is possible to demonstrate inheritance of the paternal sequences in the sorted fetal cells. Since these sequences are from chromosome 17, they are independent of fetal sex, and may be used to distinguish female fetal DNA from maternal DNA. Amplified DNA was separated by electrophoresis through ethidium bromide stained agarose gels. The DNA was transferred to nylon filters and probed using $^{32}$P labeled sequence. The maternal DNA, paternal DNA TfR$^+$ cells, and TfR$^-$ cells were then compared.

In 5 of 10 pregnant women, it was possible to show the presence of paternal sequences in the sorted candidate fetal cell population. In the other 5 women, no differences were seen between the maternal DNA and the DNA obtained from the candidate fetal cells.

EXAMPLE 8

Reconstruction Experiments using Non-Pregnant Female Blood and Added Male Cord Blood to Simulate the Presence of Fetal Cells in Maternal Blood Venous blood samples (20 ml) were collected in EDTA from healthy non-pregnant women. Umbilical cord blood samples (10 ml) were collected in EDTA from normal newborns. The mononuclear cell layer was isolated by Ficoll/Hypaque density centrifugation. Cell counts were performed with a hemocytometer. Separate aliquots of cells were made containing: 1) female cells alone; 2) female cells plus $10^2$ added male cord blood cells; 3) 3 female cells plus $10^3$ added male cord blood cells; 4) female cells plus $10^4$ added male cord blood cells; 5) female cells plus $10^5$ added male cord blood cells; 6) female cells plus $10^6$ added male cord blood cells; 7) male cord blood cells alone. The separate aliquots were then incubated with the individual monoclonal antibodies being tested. Analysis and sorting were performed using a flow cytometer. For each aliquot, a bivariate histogram was obtained, and gating parameters were established for antibody positive and antibody negative cells. The sorted cells were collected into sterile micro test tubes and frozen at −20° C. PCR amplification was performed with primers that detect a 397 bp sequence unique to the Y chromosome. The presence of a band at 397 bp in autoradiographs was used to confirm the presence of male umbilical cord blood cells in sorted samples.

FIG. 5 shows the histograms obtained when FITC-anti transferrin receptor is used. In the non-pregnant female, 0.1% of the mononuclear cells react with the antibody. In male cord blood, 24.9% of the mononuclear cells react with the antibody. With the addition of more and more umbilical cord cells to the non-pregnant female cells, and increased percentage of cells that react with the antibody is seen.

Figure 6:
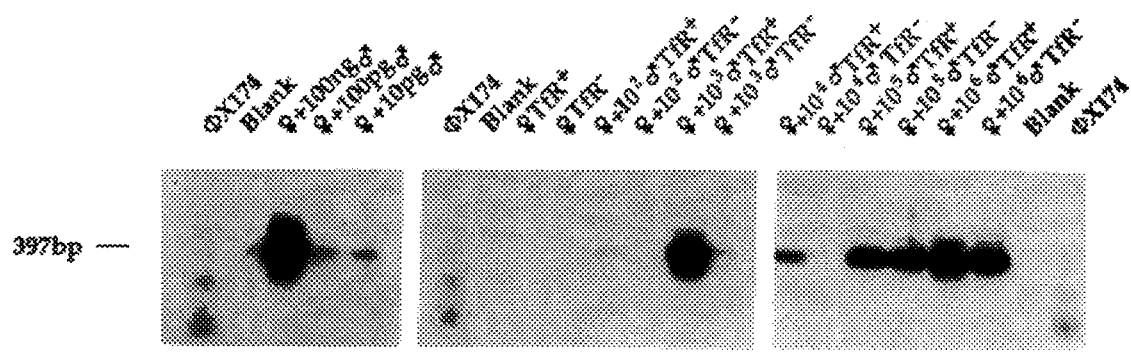
FIG. 6 is a composite autoradiograph of amplified male DNA detected in TfR cells when $10^2$–$10^6$ male cells are added to samples from non-pregnant females and in TfR⁻ cells when $10^5$–$10^6$ male cells are added to samples, from non-pregnant females.
Figure 7A:
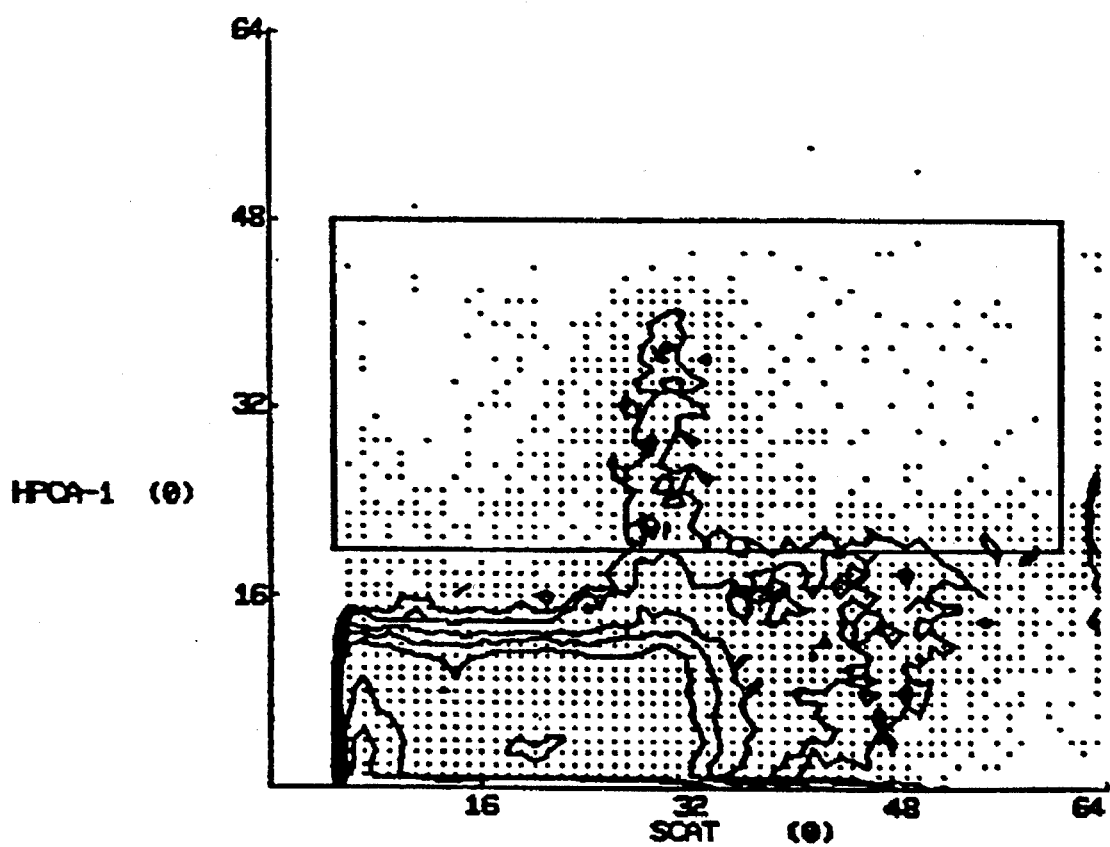
FIGS. 7A, 7B, 7C, 7D, 7E, 7F, 7G and 7H are a series of histograms obtained when anti HPCA-1 antibody was used to determine the presence of mononuclear cells in samples from nonpregnant females to which male cells have been added.
Figure 7B:
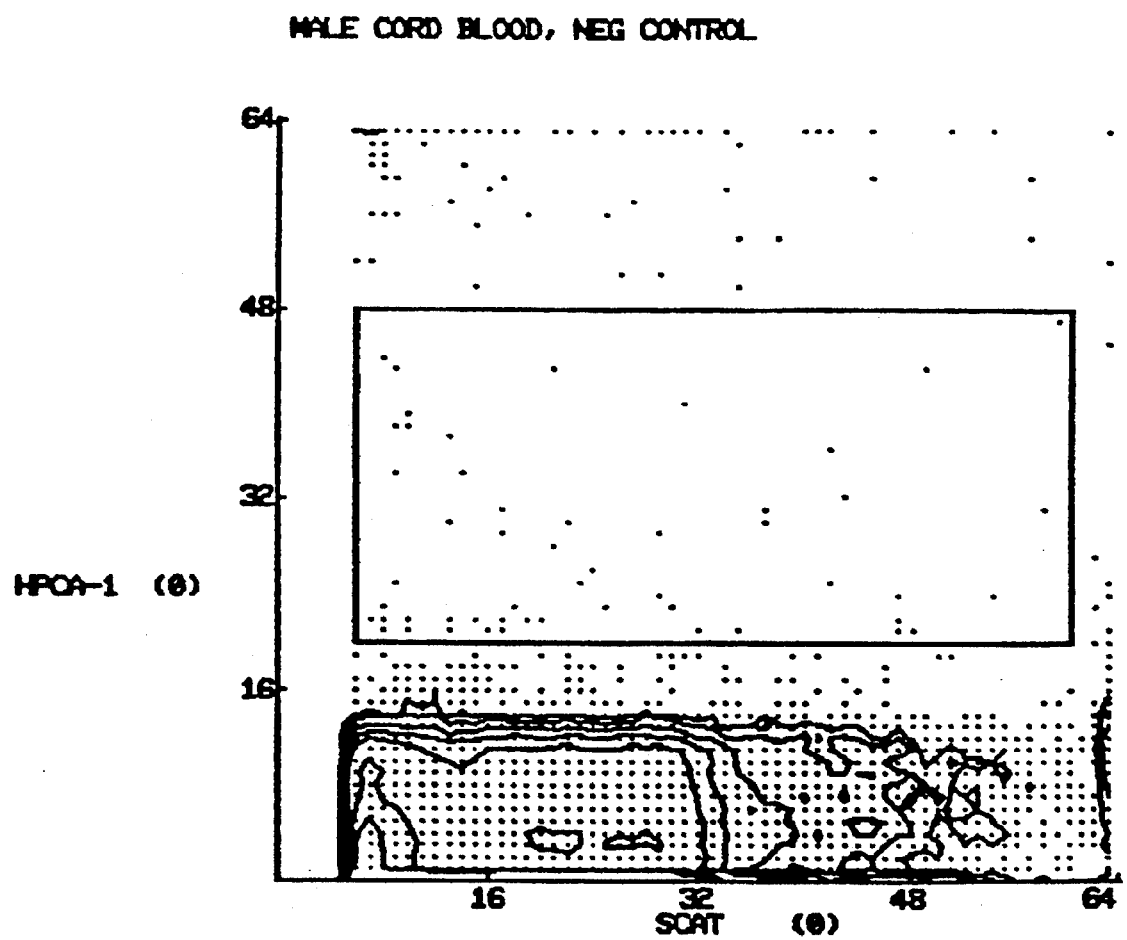
Figure 7C:
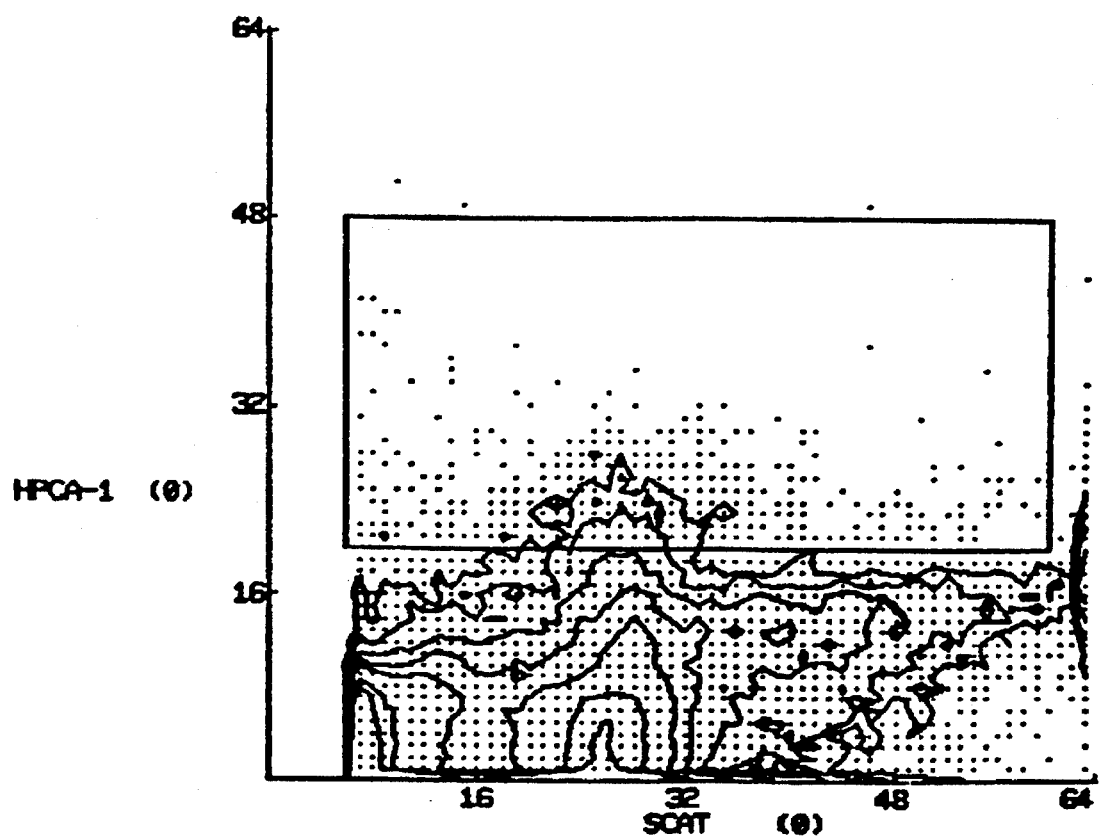
Figure 7D:
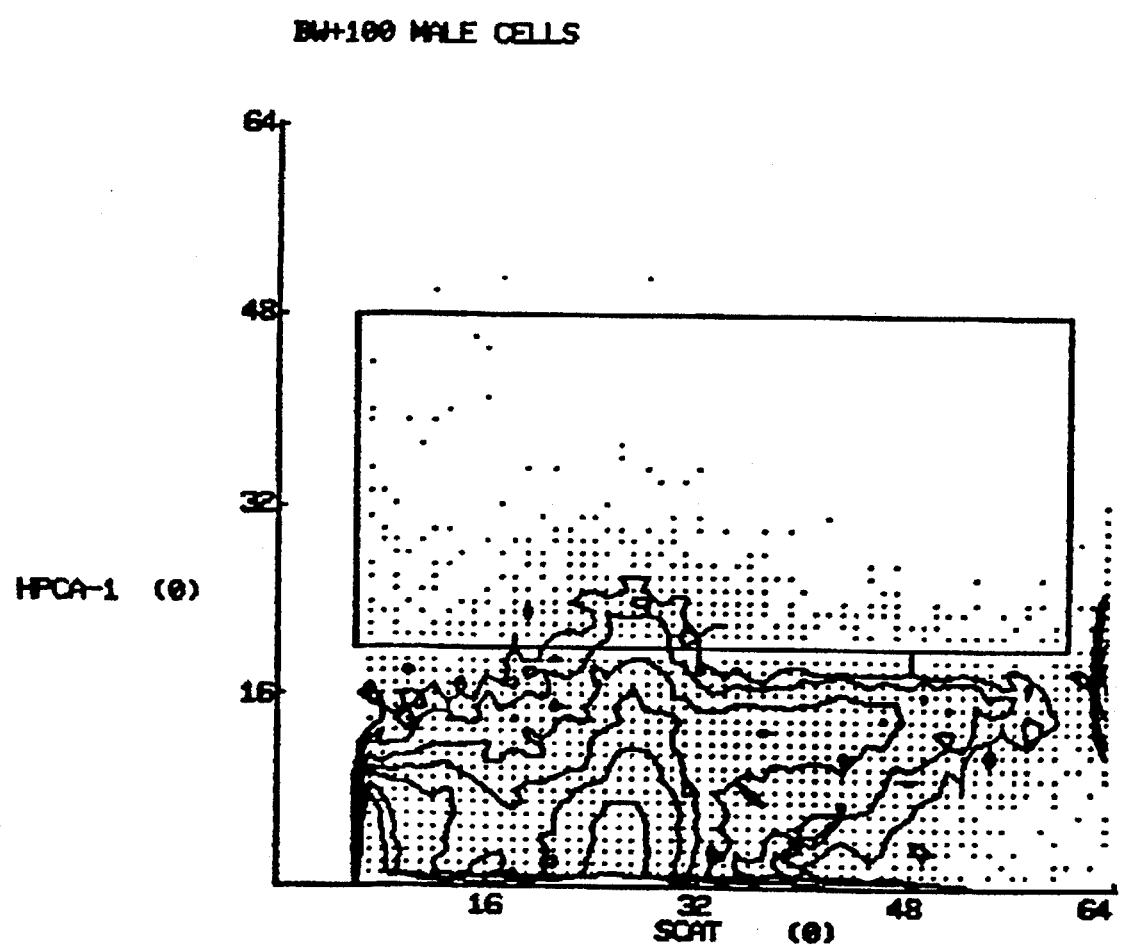
Figure 7E:
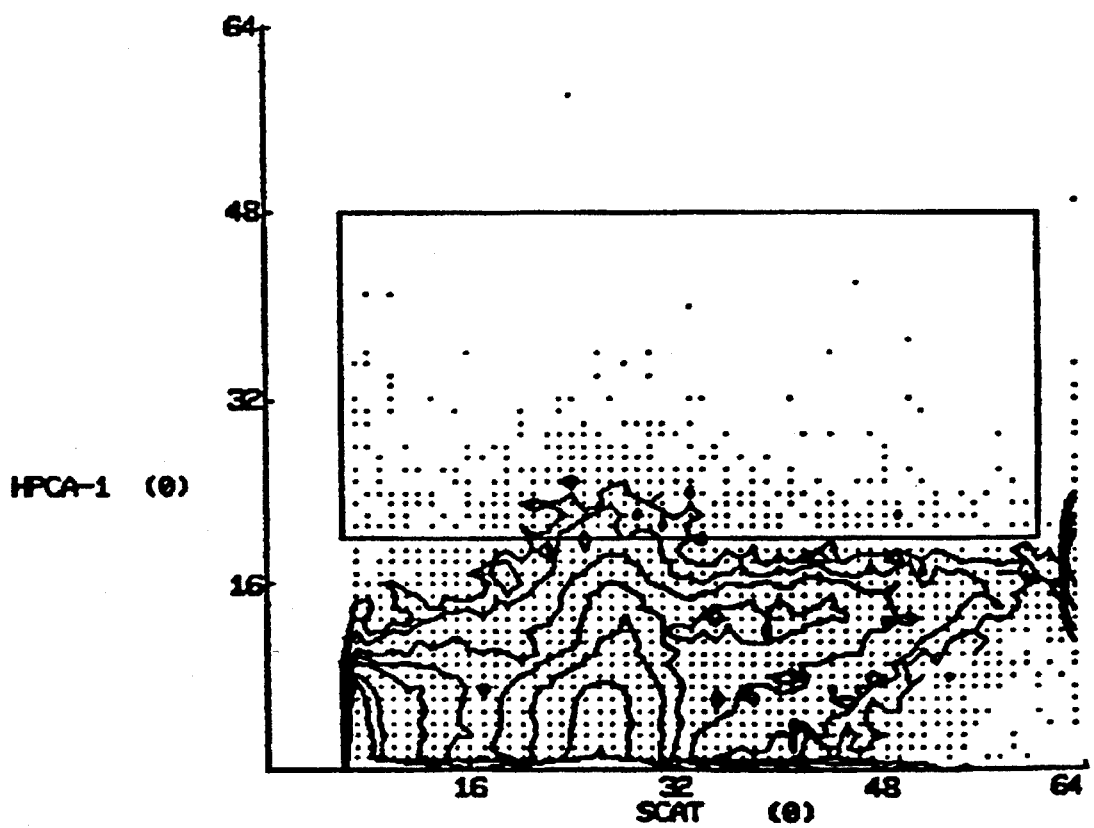
Figure 7F:
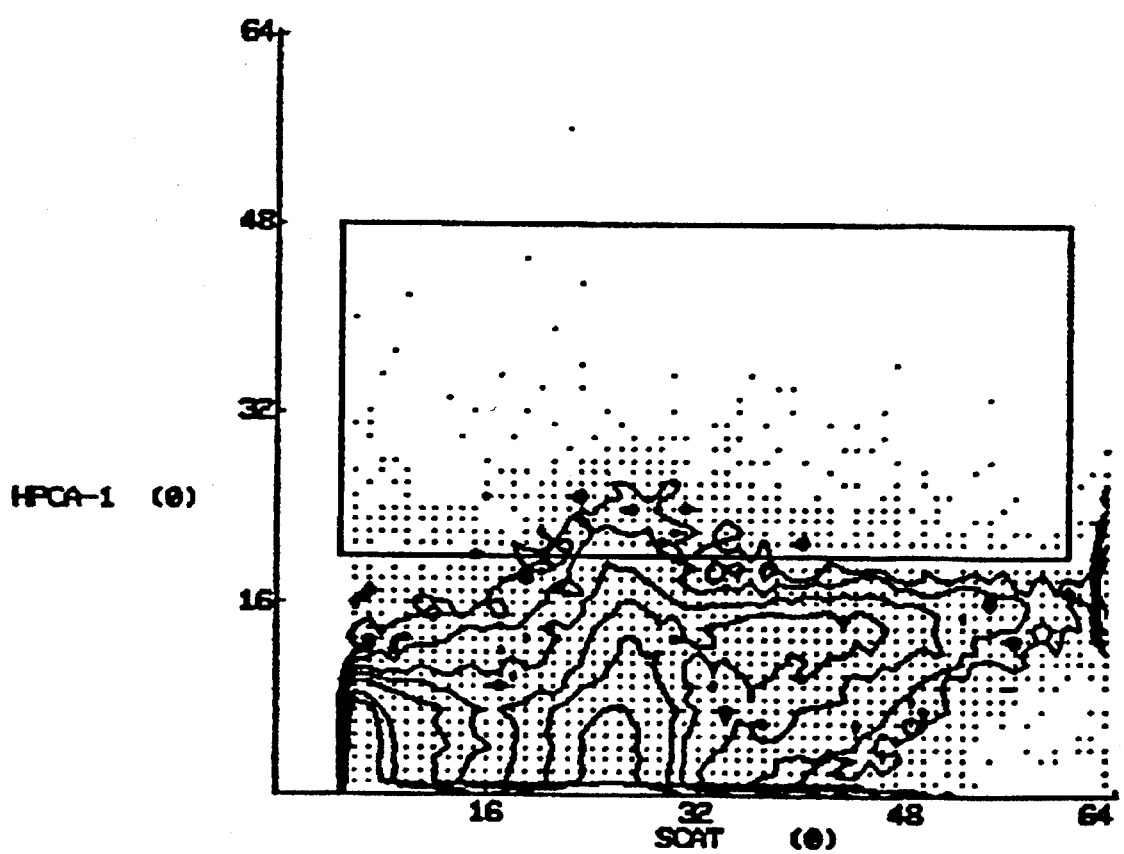
Figure 7G:
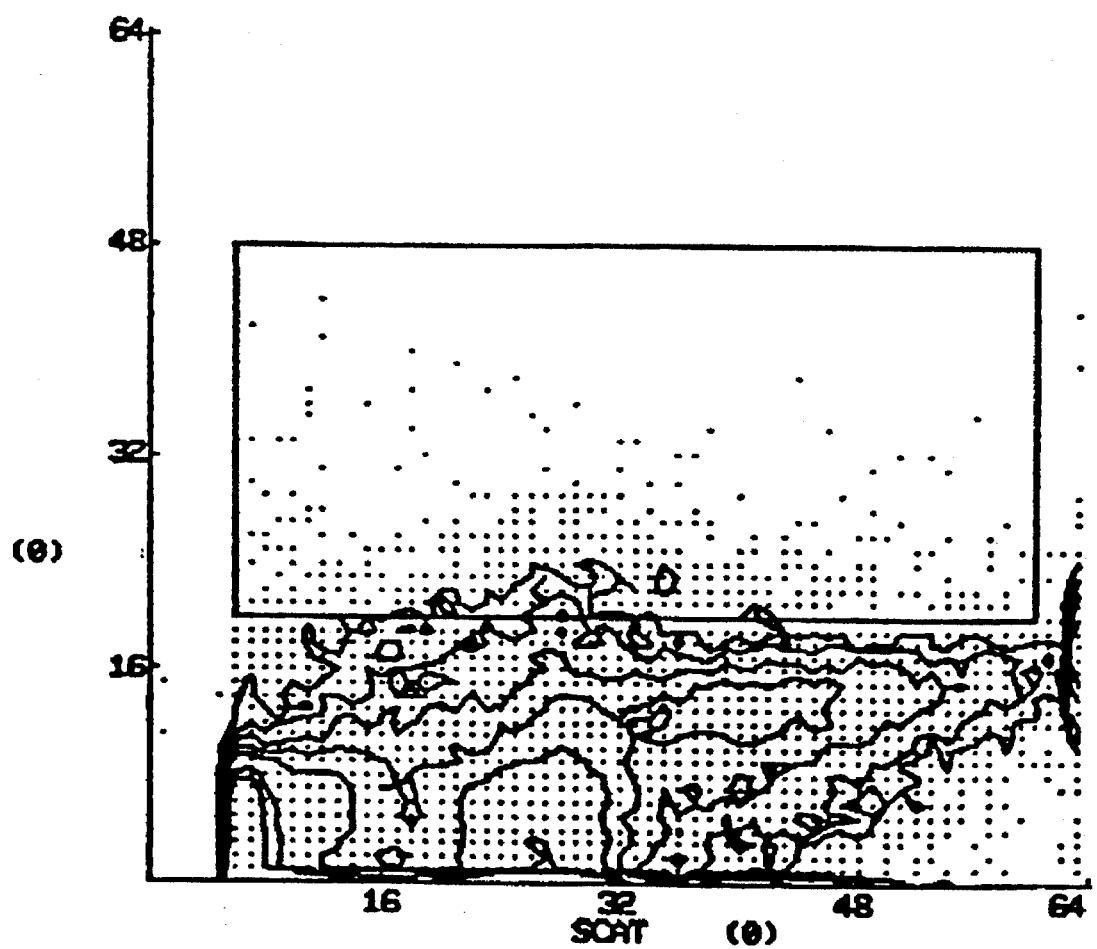
Figure 7H:
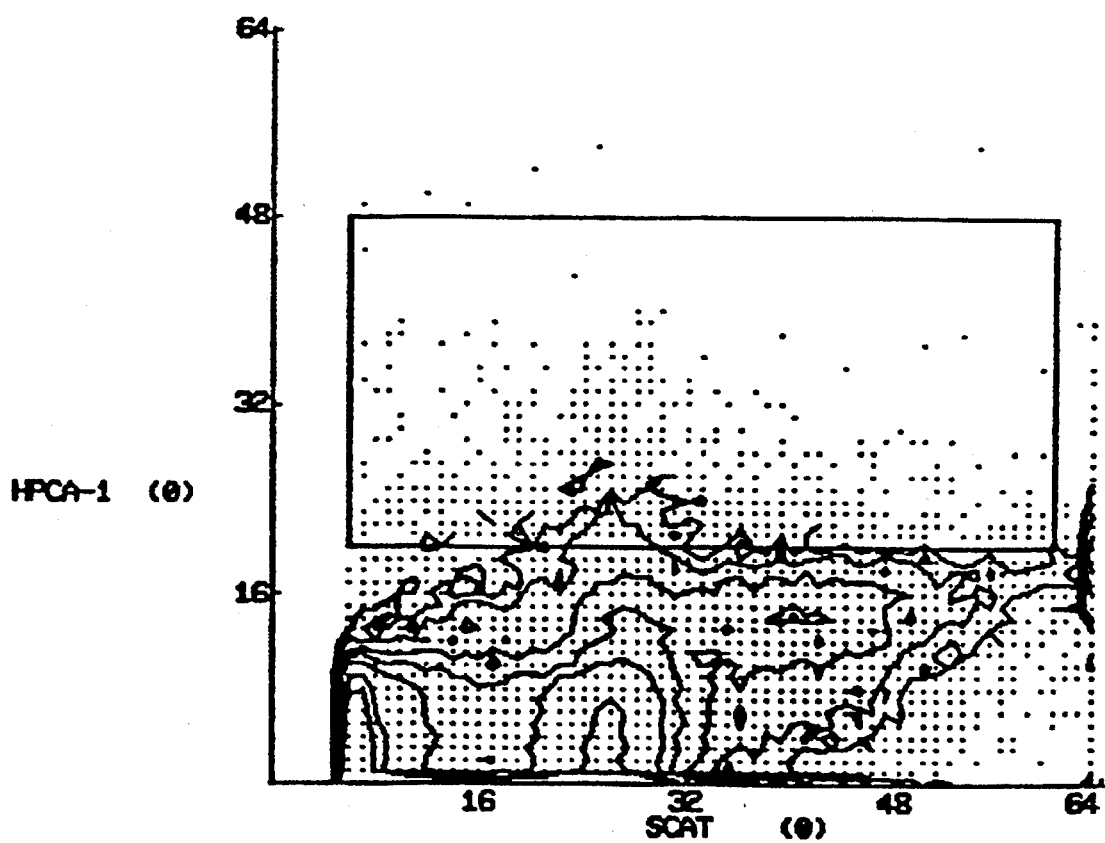

FIG. 6 shows that male DNA is detected in the TfR$^+$ cells when $10^2$–$10^6$ male cells are added. Male DNA is detected in the TfR$^-$ cells when $10^5$–$10^6$ male cells are added. This results from the presence of male white blood cells in the TfR$^-$ population.

FIG. 7 shows the histograms obtained when anti HPCA-1 antibody is used. In the non-pregnant female, 0.9% of the mononuclear cells react with antibody. In umbilical cord blood, a well-defined population of cells is seen, but the percentage is only 1.1%. Thus, the addition of umbilical cord blood cells to the nonpregnant female cells is not seen on the histograms as clearly as with the transferrin receptor antibody. An increased number of HPCA$^+$ cells were collected as the amounts of added cord blood cells increased.

In agarose gels, the 397 bp band consistent with DNA was detected in the HPCA$^+$ cells when $10^3$–$10^5$ male cells were added to the female cells. Male DNA was detected in agarose gels in the HPCA cells when $10^6$ male cells were added to the female cells.

EXAMPLE 9

In situ Hybridization using Molecular Probes Recognizing Individual Chromosomes in Flow Sorted Nucleated Erythrocytes To demonstrate diagnostic utility of the present invention, a DNA probe set was constructed of chromosome specific probes that provided both good signal to noise ratios and good spatial resolution of the fluorescent signals. Accordingly, specific probes were developed for five chromosomes frequently seen as liveborn aneuploidies; chromosomes 13, 18, 21, X and Y. A probe for chromosome 1 was used as a control. In constructing the probes, the general strategy was to identify a starting clone that mapped to the desired chromosomal region by multiple genetic and physical methods, and then to use that clone to identify a matching cosmid "contig" which was then used as a hybridization probe.

Figure 8:
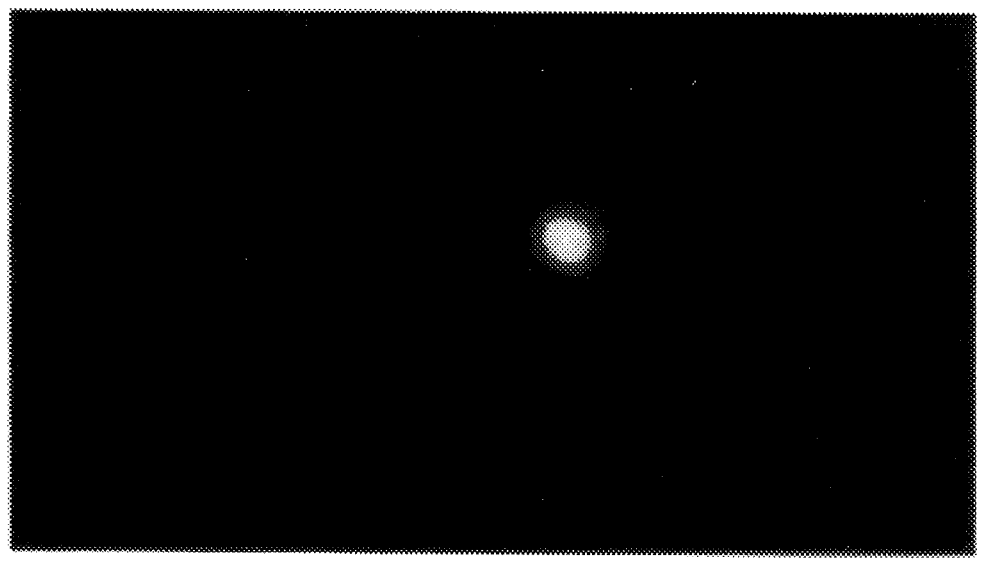
FIG. 8 is a photograph illustrating a fluorescent cell due to the positive results of in situ hybridization of the pDP97 probe for the Y chromosome to a fetal nucleated red blood cell.

Hybridization of the high copy number repeat sequences was suppressed by inclusion of total genomic human DNA, and the chromosomal specificity verified by hybridization to metaphase spreads. The probes gave sharp, punctate fluorescent signals in interphase cells that were easily discriminated and enumerated. The Y probe used in this study was pDP97, a repetitive clone (a 5.3 kb EcoRI Y fragment from cosmid Y97 subcloned into EcoRI site of pUC-13). All probes were labeled with biotin, hybridized under suppression conditions, and specific hybridization detected by conjugated strepto-avidin-FITC, which showed as a single "dot" in the FITC image. As illustrated in FIG. 8, the Y chromosome was detected by in situ hybridization of a pDP97 probe for the Y chromosome in a fetal nucleated red blood cell. Thus, prenatal diagnosis for chromosomal abnormalities could be performed on fetal cells isolated from maternal blood.

EXAMPLE 10

Detection of Fetal Hematopoietic Stem Cells in Maternal Circulation

Venous blood samples (20 ml) were collected in EDTA or citrate dextrose from healthy women with uncomplicated pregnancies, prior to invasive diagnostic procedures, at different points in gestation. The mononuclear cell layer was isolated by Ficoll/Hypaque density centrifugation and incubated with monoclonal antibodies directed against antigens expressed on the cell surface of hematopoietic progenitor cell. These antibodies are described in Example 2. The antibodies were either directly or indirectly conjugated to a fluorescent dye. Analysis and flow sorting of fluorescent cells were performed on a fluorescence-activated cell sorter. Fluroescent cells are cells that have bound antibody recognizing primitive cell surface antigens; thus, they are hematopoietic precursor cells. These cells were physically sorted into sterile micro test tubes and frozen at −20° C. Prior to polymerase chain reaction amplification, the cells were lysed by boiling. The polymerase chain reaction (PCR) was performed under standard conditions using standard reagents. The primers selected amplified material from the Y chromosome as a means of detecting male fetal cells. These primers defined a 397 base pair sequence. After PCR, the patient samples were analyzed with conventional Southern blots using a $^{32}$P labeled probe. Ethidium bromide stained agarose gels and autoradiographs were examined for the presence of the amplified 397 bp band, which was considered significant only if reagent controls did not reveal false positive amplification.

Twenty five women were studied with antibody to a human progenitor cell antigen (HPA). This antigen has been given a cluster of differentiation (CD) designation as CD34. Cells that are CD34+ are undifferentiated and represent hematopoietic stem cells. Eleven of the twenty five women whose peripheral blood was sorted have confirmed male pregnancies. In 8/11 (72%) of those women, male DNA was detected in the sorted CD34+ cells. This confirms that fetal hematopoietic stem cells are circulating in mother's blood.

Additionally, antibodies were used against the oncofetal antigen expressed in many leukemias (CALLA) to detect fetal lymphoblasts in the maternal circulation. This antibody is designated as CD10. Seventeen women have been sorted with antibody to CD10. In 8/17, evidence of male fetal DNA has been detected in CD10+ cells.

EXAMPLE 11

Additional Antibodies to Detect Fetal Hematopoietic Cells in Maternal Circulation Human fetal umbilical cord blood is being used as a source of mononuclear cells for study of fetal cell populations, in order to determine additional antibodies to detect fetal hematopoietic cells in material circulation. Pure fetal blood samples were tested from as early as 19 weeks gestation.

The mononuclear cell layer is isolated as described in example 10. Mononuclear cells are incubated with mouse monoclonal antibodies to human stem cell antigens (CD34, CD10, CD38, which recognizes myeloblasts, CD33, HLA-DR, CD36, glycophorin A, CD71, 8G12, THB-7 and others). Many of these antibodies are available directly conjugated to a fluorescent dye. If the antibody is not fluorescent, a sandwich technique is used to attach fluorescein-conjugated goat anti mouse antibody to the primary antibody.

Our data thus far has demonstrated that there are differences in the types of fetal cells present as the pregnancy proceeds. Approximately 4% of the fetal mononuclear cells are CD10+ until 34 weeks gestation. CD10+ cells are not detectable at term. Approximately 5% of fetal mononuclear cells are CD34+. Between 8 and 18% of fetal mononuclear cells are CD38+. The percentages of CD38+ cells increase during the pregnancy. Therefore, varying the type of antibody used in cell separation based on the length of gestation may help increase the isolation of fetal cells.

EXAMPLE 12

Detection of Y Chromosomal DNA Sequences in Venous Blood Samples Obtainly Only from Women Having Male Fetuses Venous blood samples (20 ml) were collected in EDTA or citrate dextrose from healthy women with uncomplicated pregnancies, prior to invasive diagnostic procedures, at different points in gestation. The mononuclear cell layer was isolated as described in Example 10. Alternatively, mononuclear cells cobld be obtained by (nonnucleated) red cell lysis buffers. In this example, the specific monoclonal antibodies chosen to label the fetal cells of interest are CD36 and glycophorin A, used singly or in combination. These antibodies are either directly or indirectly conjugated to a fluorescent dye. CD36 recognizes a cell surface antigen present on nucleated erythrocytes and monocytes, whereas glycophorin A recognizes an antigen present on erythrocytes. Fluorescent cells that have bound either or both antibodies were flow sorted; such cells were frozen and subsequently amplified for Y chromosomal sequences by the polymerase chain reaction as described in Example 10.

In a group of 18 women studies, 11 had male fetuses and 7 had female fetuses. Y chromosomal DNA sequences were detected in the cells sorted with CD36 and/or glycophorin A antibodies in 10/11 (91%) of the women having males. None of the women bearing females (0/7) had Y chromosomal DNA sequences detected. The probability of obtaining these results by chance, p=0.00025 by Fisher exact test. Thus, the antibodies CD36 and glycophorin A are particularly effective in identifying fetal nucleated cells circulating in maternal blood.

EXAMPLE 13

Detection of Fetal Cells with 47 XY +21 Karotype in Maternal Peripheral Blood A peripheral blood sample (20 ml.) was obtained from a pregnant woman at nineteen weeks of gestation. A previous ultrasound examination performed at 17 weeks gestation revealed fetal malformations consistent with a diagnosis of Down Syndrome. An amniocentesis was performed for fetal chromosome analysis and results of the karotype were 47, XY, +21.

Flow Cytometry

The woman's venous blood was collected in ethylenediamine tetraacetic acid (EDTA), diluted 1:3 with Hanks' balanced salt solution, layered over a Ficoll/Hypaque column (Pharmacia) and spun at 2000 rpm for twenty minutes at room temperature. The mononuclear cell layer was isolated, washed with phosphate buffered saline (PBS) and centrifuged at 1400 rpm for ten minutes at 4° C. The cell pellet was incubated with a 1:10 dilution of fluorescein-conjugated anti-TfR (anti CD 71) Becton-Dickinson Catalog No. 7513) in PBS on ice for thirty minutes. The cells were washed once in PBS prior to flow sorting.

Analysis and sorting were performed on a Becton-Dickinson FACS IV with a Consort 40 program as described previously (Bianchi et al., *Cytometry* 8:197–202 (1987)). The gain was standardized manually using fluorescent beads and a fluorescein isothiocyanate (FITC) conjugated antibody control, keyhole limpet hemocyanin, an antigen not expressed on human cells (Becton-Dickinson Catalog No. 9041). A small aliquot of the woman's mononuclear cells were incubated with the antibody control to determine background fluorescence. $TfR^+$ (fluorescent) and $TfR^-$ (non-fluorescent) cells were determined by physical separation on a logarithmic scale and sorted into 1.5 ml centrifuge tubes.

Fluorescence in Situ Hybridization

A solution of methanol and acetic acid (3:1) was used to fix nuclei from sorted cells to glass slides which were then stored at −20° C. (Klinger et al., *Am. J. Hum. Genet.* 51:55–65 (1992)). The contents of the entire forementioned Klinger et al. reference is expressly incorporated by reference. Prior to hybridization, slides were warmed briefly at 60° C. Control hybridizations with male lymphocytes were performed concurrently.

The probe sets used for hybridization to the Y chromosome and to chromosome 21 have been described previously (Klinger et al., cited supra, (1992)). The Y chromosome probe was labeled with biotin-dUTP (Sigma) and the chromosome 21 probe was labeled with digoxigenin-dUTP (Boehringer Mannheim). The probes were hybridized simultaneously under suppression conditions (Cremer et al., *Hum Genet* 80:235–246 (1988); Lichter et al., *Hum Genet* 80:224–234 (1988)). The Y chromosome probe was detected with avidin conjugated to Texas Red (Vector Laboratories) and the chromosome 21 probe was detected with anti-digoxigenin conjugated to fluorescein isothiocyanate (FITC) (Boehringer Mannheim). The slides were mounted in 2.33% DABCO (1,4-diazobicyclo[2.2.2]octane) (Sigma) in 100 mM Tris-HCl, pH 8.0, 90% (v/v) glycerol with 0.5 ug/ml 4,6-diamidino-2-phenyl-indole (DAPI) as a counterstain (Sigma). Slides were analyzed using a Zeiss Axioplan epifluorescence microscope. FITC and Texas Red were monitored simultaneously using a dual band pass filter set (Omega Optical, Inc., Brattleboro, Vt.). Images were captured with a cooled confocal digital camera (Photometrics Ltd., Tucson, Ariz.) and image processing was performed with software developed by Recognition Technology, Inc., (Westboro, Mass.).

Figure 9:
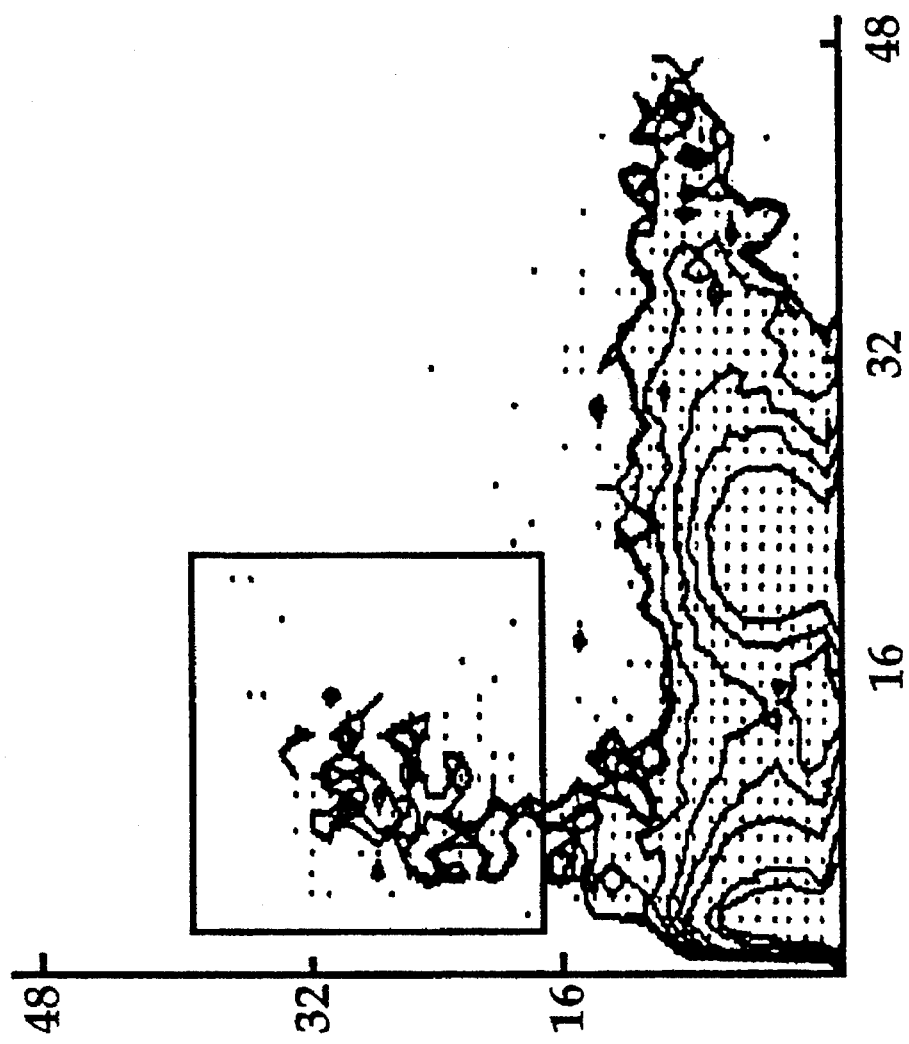
FIG. 9 is a two-dimensional bivariate histogram depicting forward angle light scatter on the X axis (an indication of cell volume) and fluorescence intensity on the Y axis (a measure of cells binding the TfR antibody. The TfR⁺ cells representing 1.3% of the maternal mononuclear cells are encased in a box.

The results of the contour plot depicting fluorescence intensity versus light scatter are shown in FIG. 9. The percentage of $TfR^+$ cells was 1.3. A total of approximately 43,000 $TfR^+$ cells and 300,000 $TfR^-$ cells were sorted.

Figure 10:
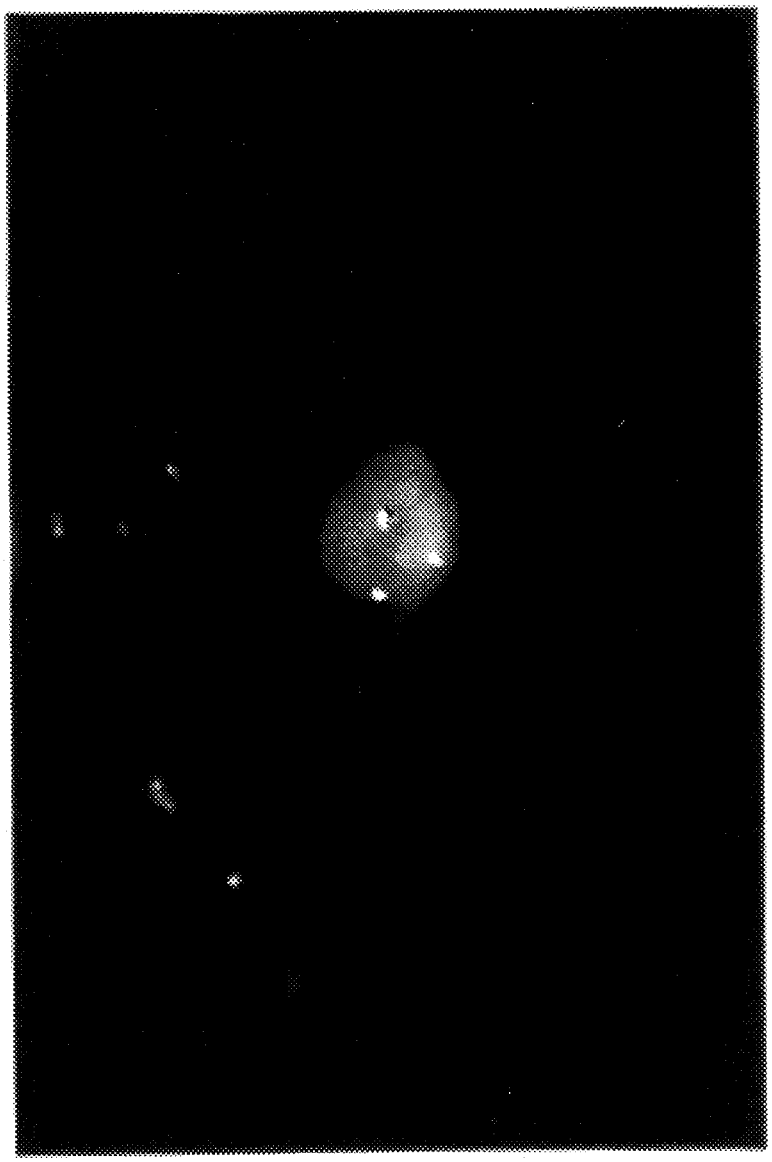
FIG. 10 is a photomicrograph of a flow-sorted interphase fetal nucleus isolated from maternal blood. The single black dot represents hybridization to the Y chromosome and the three white dots represent hybridization to the chromosome 21s. The karotype of this nucleus is 47, XY, +21.

In situ hybridization studies performed on the $TfR^-$ cells revealed the presence of numerous nuclei. Control slides prepared from male lymphocytes gave bright signals with both the 21 and Y probes. The nuclei from $TfR^-$ cells that hybridized to the probes were exclusively maternal, with two signals for chromosome 21 and no signal with the Y. The majority of the sorted cells in the $TfR^+$ fraction did not hybridize, due to the fact that most of them were reticulocytes, which are anucleate. Most of the nuclei present were in a few giant clumps that had retained large amounts of cytoplasm. Of the few $TfR^+$ cells that did hybridize, FITC and Texas Red signals were generally weak. There were three nuclei with one Texas Red and three FITC signals, consistent with the presence of one Y chromosome and three copies of chromosome 21 (FIG. 10). The remainder of the data are summarized as follows.

Results of hybridization studies on scored cells:

|  | Texax Red (Y) | FITC (21) | Number of Cells |
|---|---|---|---|
| Number of signals | 1 | 3 | 3 |
|  | 1 | 0 | 8 |
|  | 0 | 3 | 1 |
|  | 1 | 1 | 1 |
|  |  |  | 13 |
|  |  | Uninformative | 15 |
|  |  |  | 28 |

EQUIVALENTS

Those skilled in the art will recognize, or be able to ascertain using no more than routine experimentation, many equivalents to the specific embodiments of the invention described herein. Such equivalents are intended to be encompassed by the following claims.

I claim:

1. A noninvasive method for facilitating prenatal diagnosis of a chromosomal abnormality in a fetus, comprising:
    obtaining a peripheral blood sample from a pregnant woman;
    treating the peripheral blood sample to produce an enriched blood sample enriched in fetal nucleated erythrocytes; and
    performing in situ hybridization on the enriched blood sample with a chromosome specific probe or a probe specific for abnormal chromosomal DNA to generate spatially resolved signals in individual chromosomes of interphase cells such that diagnosis of a chromosomal abnormality in the fetus is facilitated on the basis of the generated signals.

2. The method of claim 1 wherein the chromosomal abnormality is an aneuploidy.

3. The method of claim 1 wherein the in situ hybridization is fluorescent in situ hybridization.

4. The method of claim 1 wherein the probe is hybridizable to fetal DNA of interest contained in a chromosome selected from the group consisting of chromosomes 13, 18, 21, X, and Y.

5. The method of any one of claims 1-4 wherein the sample is treated in a multistep enrichment process for fetal nucleated erythrocytes.

6. The method of claim 1 wherein the multistep enrichment includes the separation of non-nucleated cells from nucleated cells in the peripheral blood sample from the pregnant woman forming a nucleated cell enriched sample and the treatment of the nucleated cell enriched sample such that the proportion of fetal cells in the sample is increased with respect to the proportion of cells from the pregnant woman forming a sample enriched in fetal nucleated erythrocytes.

7. The method of claim 1 wherein the peripheral blood sample from the pregnant woman is enriched in fetal nucleated cells using density gradient centrifugation.

8. The method of claim 1 wherein the peripheral blood sample from the pregnant woman is enriched in fetal nucleated cells by lysing nonnucleated cells.

9. The method of claim 1 wherein the peripheral blood sample from the pregnant woman is treated for enrichment for fetal nucleated erythrocytes using only a single fetal-specific monoclonal antibody.

10. The method of claim 1 wherein the peripheral blood sample from the pregnant woman is treated for enrichment for fetal nucleated erythrocytes using at least one fetal-specific monoclonal antibody.

11. The method of claim 1 wherein in situ hybridization is performed on a solid support.

12. The method of claims 1 wherein the peripheral blood sample from the pregnant woman is treated by contacting it with a first monoclonal antibody which recognizes fetal nucleated erythrocytes but not cells derived from the peripheral blood sample from the pregnant woman and/or a second monoclonal antibody which recognizes cells derived from the peripheral blood sample from the pregnant woman but not fetal nucleated erythrocytes, under conditions appropriate for antibody binding thereby producing fetal nucleated erythrocyte-first monoclonal antibody complexes and/or pregnant woman cell-second monoclonal antibody complexes, respectively, and
    separating fetal nucleated erythrocyte-first monoclonal antibody complexes from pregnant woman cells and/or separating pregnant woman cell-second monoclonal antibody complexes from fetal nucleated erythrocytes thereby separating fetal nucleated erythrocytes from cells derived from the peripheral blood sample from the pregnant woman.

13. The method of claim 12 wherein the first and/or second monoclonal antibody are attached to a solid support.

14. The method of claim 12 wherein the peripheral blood sample from the pregnant woman is obtained when the gestational age of the fetus is about fifteen to seventeen weeks.

15. The method of claim 14 wherein the peripheral blood sample from the pregnant woman is obtained when the gestational age of the fetus is about sixteen weeks.

16. The method of claim 13 wherein the solid support is a magnetizable bead.

17. The method of any of claims 1, 3 or 5–16, wherein the probe is hybridizable to fetal DNA of interest contained in a Y chromosome.

18. The method of any of claims 1, 3 or 5–16, wherein the probe is hybridizable to fetal DNA of interest which is associated with a disease.

19. The method of claim 18 wherein the disease is cystic fibrosis.

20. The method of claim 18 wherein the disease as Duchenne muscular dystrophy.

21. The method of claim 18 wherein the disease is hemophilia A.

22. The method of claim 18 wherein the disease is Gaucher's disease.

23. The method of claim 18 wherein the disease is sickle cell anemia.

24. The method of claim 18 wherein the disease is β thalassemia.

25. The method of claim 18 wherein the disease phenylketonuria.

26. The method of claim 5, wherein the probe is hybridizable to fetal DNA of interest contained in a Y chromosome.

* * * * *